United States Patent [19]
Moriuchi

[11] Patent Number: 6,013,854
[45] Date of Patent: *Jan. 11, 2000

[54] INDWELLING STENT AND THE METHOD FOR MANUFACTURING THE SAME

[75] Inventor: Yousuke Moriuchi, Fujinomiya, Japan

[73] Assignee: Terumo Kabushiki Kaisha, Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/491,572

[22] Filed: Jun. 16, 1995

[30] Foreign Application Priority Data

| Jun. 17, 1994 | [JP] | Japan | 6-159374 |
| Jan. 27, 1995 | [JP] | Japan | 6-031761 |
| Feb. 16, 1995 | [JP] | Japan | 6-053593 |

[51] Int. Cl.⁷ .............. A61F 2/06; A61M 29/00; A61B 17/00
[52] U.S. Cl. .................. 623/11; 623/1; 623/12; 606/194; 606/198
[58] Field of Search .............. 623/1, 12; 606/194, 606/198

[56] References Cited

U.S. PATENT DOCUMENTS

| 4,355,664 | 10/1982 | Cook et al. . |
| 4,386,629 | 6/1983 | Cook et al. . |
| 4,390,599 | 6/1983 | Broyles . |
| 4,432,824 | 2/1984 | Cook et al. . |
| 4,553,545 | 11/1985 | Maass et al. ............ 128/341 |
| 4,580,568 | 4/1986 | Gianturco . |
| 4,732,152 | 3/1988 | Wallstén et al. . |
| 4,733,665 | 3/1988 | Palmaz . |
| 4,776,337 | 10/1988 | Palmaz . |
| 5,015,253 | 5/1991 | MacGregor ............ 623/1 |
| 5,104,404 | 4/1992 | Wolff ............ 623/1 |
| 5,133,732 | 7/1992 | Wiktor . |
| 5,147,370 | 9/1992 | McNamara et al. ............ 623/1 |
| 5,158,548 | 10/1992 | Lau et al. ............ 604/96 |
| 5,195,984 | 3/1993 | Schatz . |
| 5,226,913 | 7/1993 | Pinchuk ............ 623/1 |
| 5,314,472 | 5/1994 | Fontaine ............ 623/12 |
| 5,354,309 | 10/1994 | Schnepp-Pesch et al. . |
| 5,356,433 | 10/1994 | Rowland et al. ............ 623/1 |
| 5,421,955 | 6/1995 | Lau et al. . |
| 5,449,373 | 9/1995 | Pinchasik et al. ............ 623/1 |
| 5,665,115 | 9/1997 | Cragg ............ 623/1 |

FOREIGN PATENT DOCUMENTS

| 0 346 564 | 12/1989 | European Pat. Off. . |
| 0 364 787 | 4/1990 | European Pat. Off. . |
| WO91/17789 | 11/1991 | European Pat. Off. . |
| 0 596 145 | 5/1994 | European Pat. Off. . |
| 9417754 | 8/1994 | WIPO ............ 623/1 |

Primary Examiner—David J. Isabella
Assistant Examiner—Choon P. Koh
Attorney, Agent, or Firm—Burns, Doane, Swecker & Mathis, LLP

[57] ABSTRACT

One embodiment of a stent includes a cylindrical openwork frame having holes defined by side frame segments and middle frame segments, and notches defined by the side frame segments. This stent is made of a super elastic metal as a single piece without an abrupt change in the physical property of the stent. Another embodiment of the stent is made of wires in the shape of a substantially circular cylinder. The wires forming the stent are made thicker in the middle portion and thinner in both end portions. A stenosis-treating device includes an indwelling stent, a tubular sheath which holds the stent in a compressed state, a balloon catheter which is passed through the sheath and which has a dilatation balloon, and a projection at the rear of the portion of the sheath in which the stent is held which comes into contact with the rear end of the stent when the sheath is moved rearward and lets the stent out of the front end of the sheath.

16 Claims, 19 Drawing Sheets

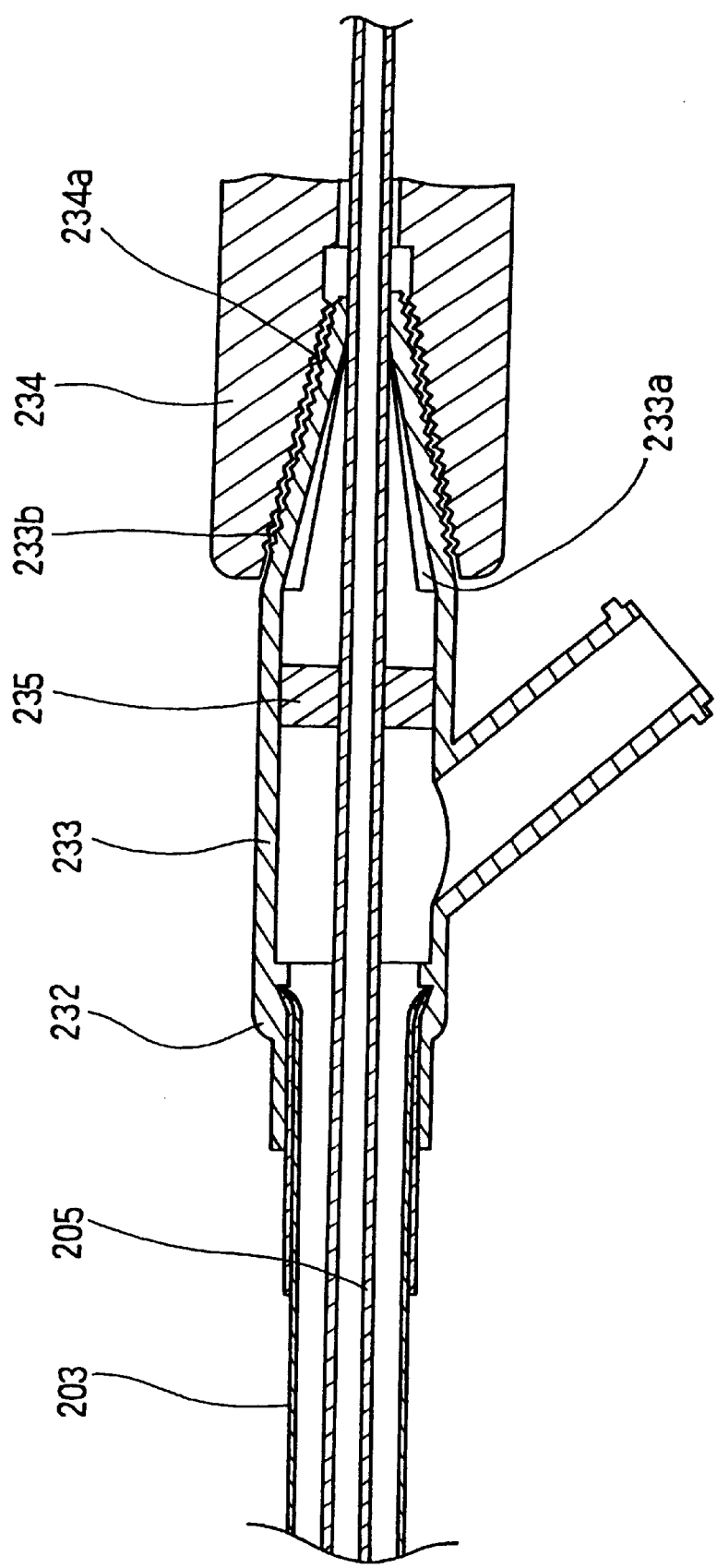

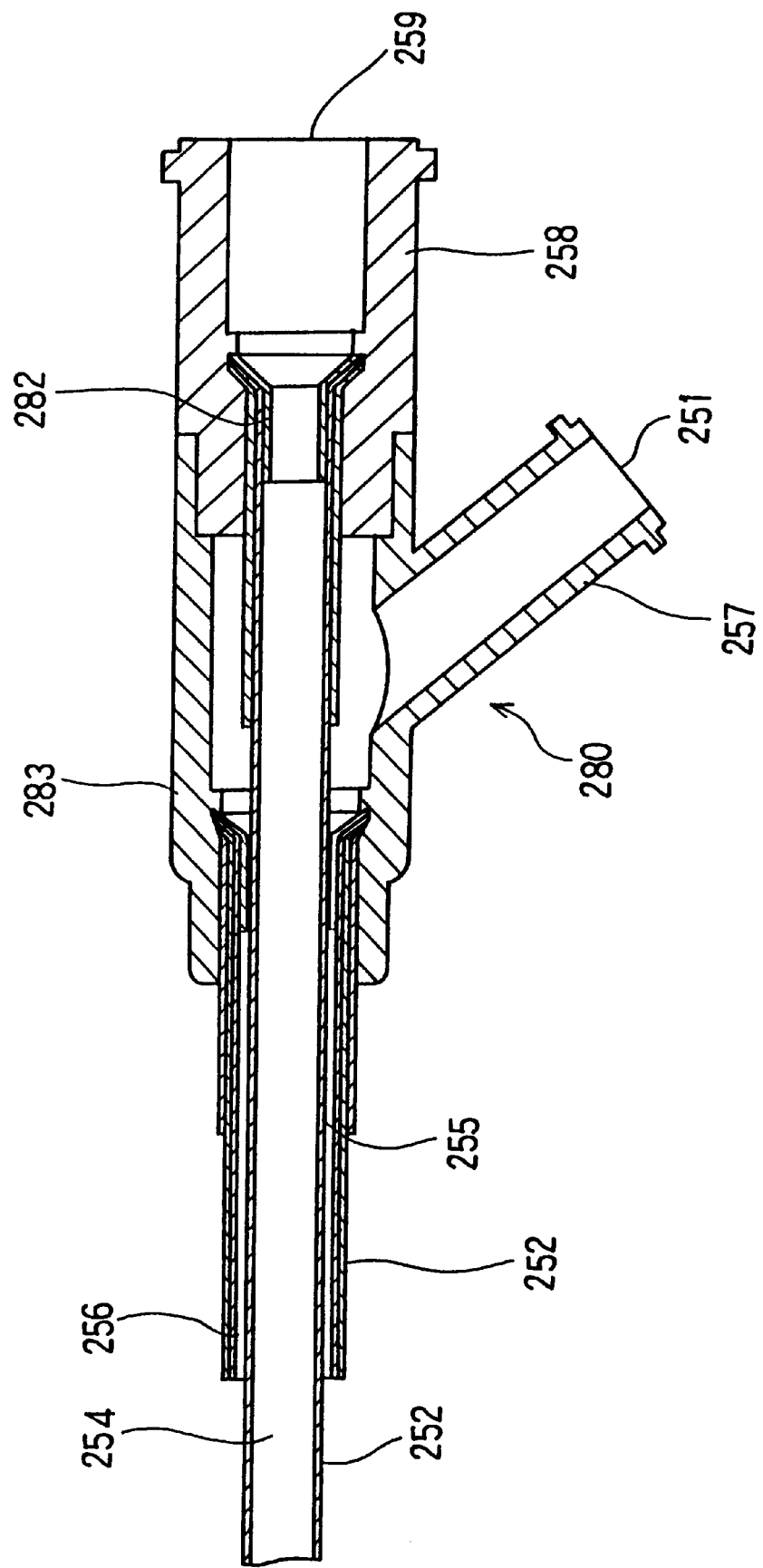

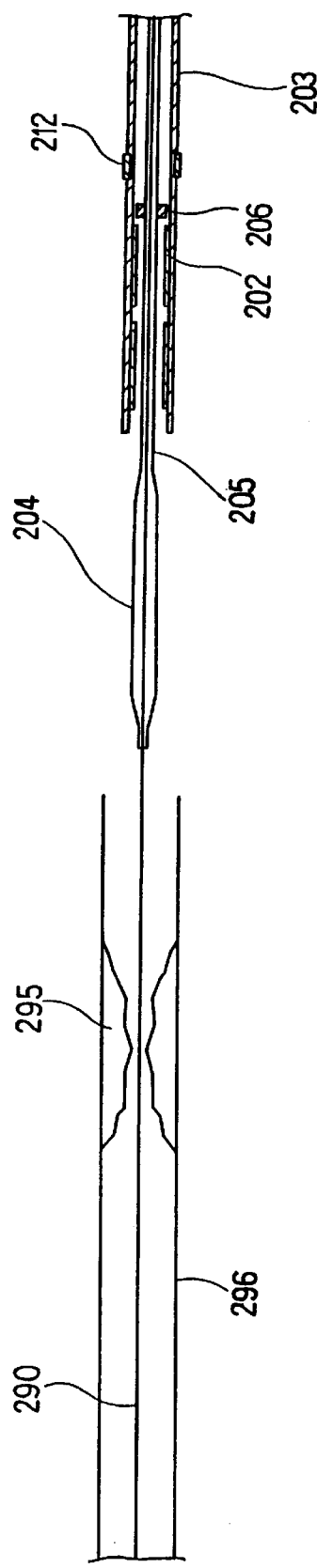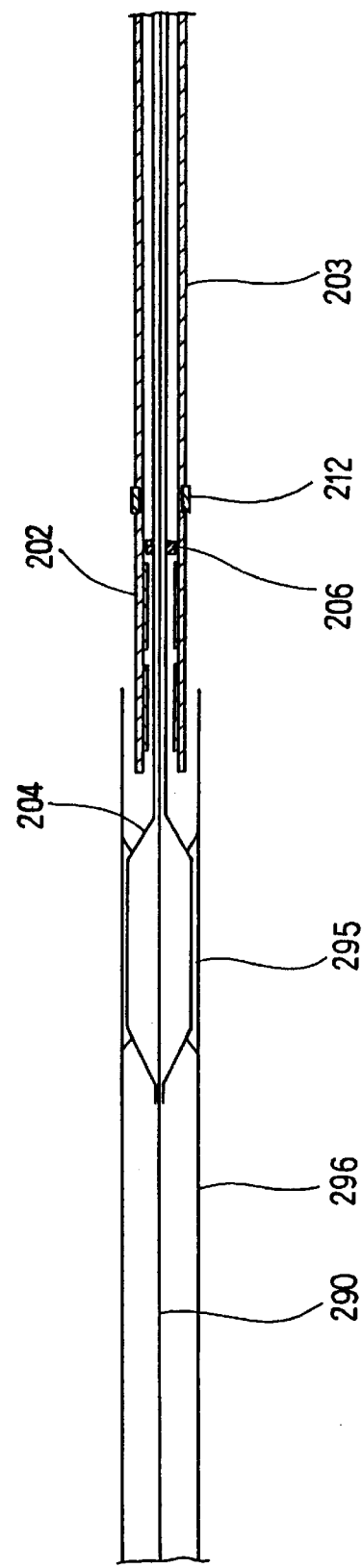
FIG. 17(a)
FIG. 17(b)

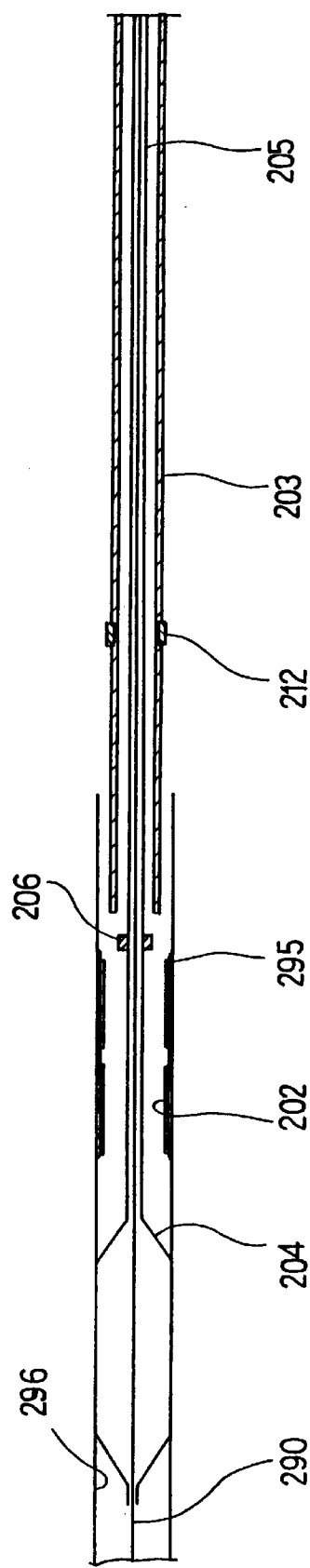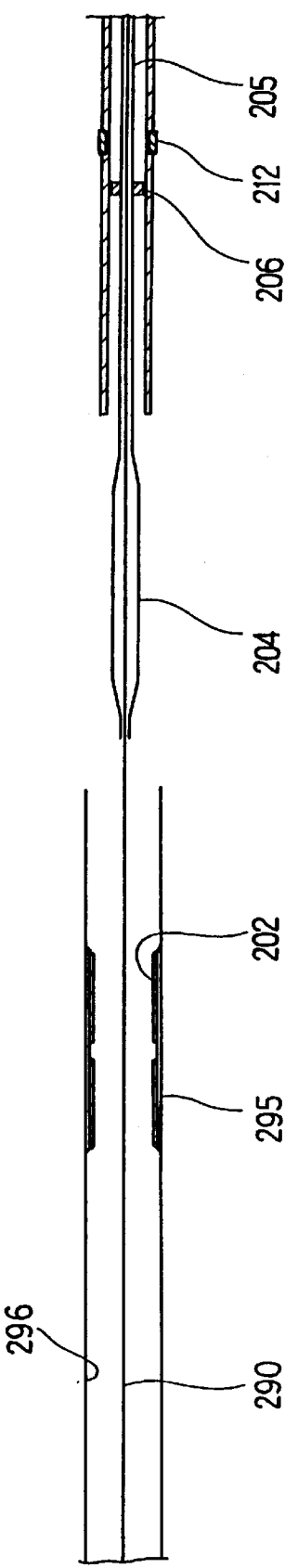

40  41

50  51

INDWELLING STENT AND THE METHOD FOR MANUFACTURING THE SAME

BACKGROUND OF THE INVENTION

This invention relates to an indwelling stent used to ameliorate a stenosed part ocurring in a blood vessel, bile duct, trachea, esophagus, ureter, and other organs in the body, and the method for manufacturing the stent.

Many types of stents are hitherto proposed to maintain the openness of a vessel or a passageway.

Those stents can be divided into two types: self-expandable stents and balloon-expandable stents.

A balloon-expandable stent does not have a capability of expanding by itself. This type of stent is put in an intended stenosed part of the body by inserting a stent into the stenosed part and inflating the balloon in the stent to expand the stent (plastic deibrmation) dilating the stenosed part. Thus, this type of stent needs the expanding operation.

A self-expandable stent, on the other hand, has capability of expanding by itseff from a compressed state. This type of stent is put in an intended stenosed part of the body by inserting a stent in a compressed state into the stenosed part and removing the force maintaining the stent in the compressed state, fbr example, by holding a stent in a compressed state in a tube of a smaller outside diameter than the inner diameter of the intended stenosed part, advancing the front end portion of the tube near the stenosed part, and pushing the stent into the stenosed part out of the tube. The stent, released from the confinement of the tube, expands to resume the original shape, and dilates the stenosed part and is securely fixed in the part. This type of stent thus does not need the expanding operation, and the insertion operation of a stent is made easier.

Many type of self-expandable stents are hitherto proposed. Specifically, a super elastic metal stent is shown in J.P.B 5-43392 gazette. The catheter shown in J.P.B 5-43392 has a sheath which covers the outside she of the catheter on which it is placed, and has a stent (device fbr dilating a stenosed part) held between the front end portion of the catheter and that of the sheath. The stent used is such that the deformation both before and after it is put in the body is within the super elastic range. The shapes of the stent shown as usable are a coil (spiral), circular cylinder, roll, stepped pipe, high-order coil, flat-spring coil, cage, or mesh.

Thus being made of a super elastic metal which exhibits a super elastic property both before and after being put in the body, the stent shown in J.P.B 5-43392 is easy to insert into a stenosed part, and can continue to dilate the stenosed part for a long period because the stent steadily exhibits the super elastic property.

However, when the stent in the shape descn bed above expands, the ends of the stent move in the stenosed part. For example, a stent in the shape of a coil becomes shorter in the direction of the axis when expanded, and hence the ends of the stent moves toward each other. A stent in the shape of a roll on the other hand, does not change lengthwise in the direction of the axis, but the distance between the corners of each end of the stent changes as the stent unwinds. This move of the stent in the stenosed part can damage the inside surface of a body wall, and the damage can cause a new stenosis.

A stent in the shape of a simple circular cylinder has no problems as described above, but it is not easy to compress to a smaller outside diameter, and hence difficult to insert into a narrow stenosed part A stent in the shape of a stepped pipe is also difficult to compress to a smaller diameter, and further can hinder the blood flow and cause a new stenosis because of the parts projecting inward.

A stent in the shape of a cage or mesh is not easy to make of a super elastic metal. Moreover, the appropriate control of the resilience of the stent is very difficult, and this makes it difficult to determine the shape (dimensions) of the stent.

The first object of this invention is to provide an indwelling stent which is made of a super elastic metal exhibiting a super elastic property both in and out the body, easy to put in a stenosed part, does not hurt the body tissue when it expands in the stenosed part, and can reliably dilate the stenosed part and maintain the dilated state, and a method fbr manufacturing the stent.

Another self-expandable stent is shown in J.P.B 4-32662 gazette. This stent 30 is made of zigzags consisting of a plurality of straight segments and forming a closed loop (cylinder) as shown in FIG. 21. This stent has a problem that the entire stent becomes too rigid when the straight segments are made long in order to use it for a long stenosed part. Further, when two or more stents are put in a stenosed part as shown in FIG. 22, the part can rupture because of a too-large dilating power, the operation fbr putting in the stents is difficult, and the stents can move out of place.

The stent 40 shown in J.U.A 4-25755 is made by connecting two or more stents end to end by means of wires 41 as shown in FIG. 23 so that it can be put in a long stenosed part. Since individual stents constituting the stent 40 are independent, the stent 40 does not have a flexibility to bend along the sharply curved stenosed part.

The stent 50 shown in J.P.A 1-14506 is formed by a helically wound zigzag wire as shown in FIG. 24. This stent 50 can maintain the openness of even a bending stenosed part along the bend. However, since this stent 50 is made of a wire of a uniform rigidity, the dilating and maintaining force against the inside surface of a body wall is the same.

The degree of narrowing of a stenosed part 61 of a hollow organ or body cavity, specifially a blood vessel 61, is generally higher at the middle portion and becomes gradually lower toward the ends as shown in FIG. 7. Moreover, blood vessels 60 are straight only in a small part of them and bend in greater or lesser degree in almost all part of them.

If a stent with a uniform rigidity is put in a stenosed part, the ends of the stent can stimulate or hurt the endothelial cells to induce a hyperplasia and cause a stenosis again, especially when the rigidity is made high to dilate the stenosed part. If the rigidity is made low 80 as to give the stent an adequate flexibility, on the other hand, the stent may not reliably dilate the stenosed part.

The second object of this invention is to provide an indwelling stent whose middle portion has an adequate rigidity to dilate the intended stenosed part and maintain the openness and whose ends are flexible enough to bend along the bend of the body part without stimnulating the endothelial cells and causing a stenosis and which stably indwells the stenosed part without shifting out of place can be easily put in a stenosed part.

As described above, there are two type of stents: balloon-expandable stent and self-expandable stent.

A boon-expandable stent does not have a capability of expanding by itself, and is put in a stenosed part, fbr example, by inserting a stent into the intended stenosed part, positioning a balloon inside the stent, and inflating the balloon to expand the stent (plastic deformation) by the expansive of the balloon to secure the stent in close contact with the inside surface of the stenosed part.

Though this type of stent requires the operation for expanding the stent as described above, this is not so serious a problem, because the operation for expanding the stent can be accomplished comparatively easily by holding the stent around the deflated balloon. However, in this type of stent does not have an expanding resilience by itself, the inside diameter becomes smaller over time because of the pressure of the body part such as a blood vessel, causing a constriction again.

A self-expandable stent, on the other hand, has a capability of expanding by itself. This type of stent is put in the intended stenosed part of the body by inserting a stent in a compressed state into the stenosed part and removing the force maintaining the stent in the compressed state, fbr example, by holding a stent in a compressed state in a tube of a smaller outside diameter than the inner diameter of the intended stenosed part, advancing the front end portion of the tube near the stenosed part, and pushing the stent into the stenosed part out of the tube. The pushed out stent, released from the confinement of the tube, expands to resume the original shape. The stent thus dilates the stenosed part and is securely fixed in the part.

Thus having a capability of expanding by itself, this type of stent does not require the expanding operation, and has no problem that the diameter becomes gradually smaller over time because of the pressure of the body part, causing the recurrence of the stenosis.

This type of stent, on the other hand, is difficult to put in the intended stenosed part because of its expanding resilience. Accurate positioning of the stent is very difficult especially in thin, sharply bending blood vessels such as coronary arteries in which a flexible stent-inserting device (sheath and catheter) must be used.

A conventional stent-inserting device fbr a self-expandable stent is shown in FIG. 25 (J.P.A 62-501271).

This device comprises a probe 70, a catheter the front end portion of which is made in a double-wall structure by folding the wall inside out at the front end, the end 71a of the inside wall being attached to the probe 70, and a stent 72 held between the probe 70 and the catheter 71. This device is so constructed that the stent 72 is pushed out by the catheter 71 into the stenosed part when the probe 70 is moved frontward in the direction of the axis. This structure, however, is difficult to use in thin, sharply bending coronary arteries, because the portion in which the stent is held becomes rigid. Further, no device is made to accurately position the stent in a stenosed part in thin, sharply bending coronary arteries. Furthermore, since the very thin catheter must be folded inside out, this stent-inserting device is difficult to manufacture.

As described above, until today, there is no stentinserting device (assembly) which can put a self-expandable stent accurately in a stenosed part in thin, sharply bending hollow organs such as coronary arteries.

Therefore, the third object of this invention is to provide a stenosis-treating device which can put a selfexpandable stent easily and accurately in a stenosed part in thin, sharply bending hollow organs such as coronary arteries.

SUMMARY OF THE INVENTION

The first object is attained by an indwelling stent of this invention which is made of a super elastic metal exhibiting a super elastic property both in and out the body in a substantially circular cylinder, has a high deformability to deform in the direction to which the outside diameter becomes smaller when a pressure is applied provided by a plurality of notches or holes made in the cylindrical wall, and is as a single piece without abrupt change in the physical property within it.

The first object is attained by a method of this invention for manufacturing the above stent, characterized by comprising a step of preparing a super elastic metal pipe of an outside diameter suited fbr the part of the body in which the sent is put, and a step of making a plurality of notches or holes in the cylindrical wall of the pipe by removing unnecessary parts in the cylindrical wall.

The second object is attained by an indwelling stent of this invention which is made of wires in a substantially circular cylinder and is compressed to a smaller diameter when being put in the body and expands to the uncompressed shape after being put in the body, characterized by that the wires are made thicker in the middle portion than in both end portions of the stent.

The third object is attained by the stenosis-treating device of this invention comprising an indwelling stent which is made of a substantially circular cylinder and is compressed to a smaller outside diameter when being put in the body and expands to the uncompressed shape after being put in the body, a tubular sheath which holds said stent in a compressed state in it, and a balloon catheter which is passed through the sheath and the stent and has a dilatation balloon equipped at the portion extending beyond the front end of the sheath, the balloon catheter having a projection at the rear of the portion of the sheath in which the stent is held which comes into contact with the rear end of said stent held in said sheath and let the stent out of the front end of the sheath when the sheath is moved rearward.

BRIEF DESCRIPTION OF THE DRAWINGS

FIG. 15 is a sectional view of the Y-shaped connector of the sheath as a component of the stenosis-treating device of this invention and its vicinity.

FIG. 16 is a sectional view of the branched hub of the balloon catheter as a component of the stenosis-treating device of this invention and its vicinity.

FIGS. 17(a) and 17(b) are diagrammatic sectional views for illustrating the function of the stenosis-treating device of this invention.

FIGS. 19(a) and 19(b) are diagrammatic sectional views for illustrating the function of the stenosis-treating device of this invention.

DETAILED DESCRIPTION OF THE PREFERRED EMBODIMENTS

Figure 1:
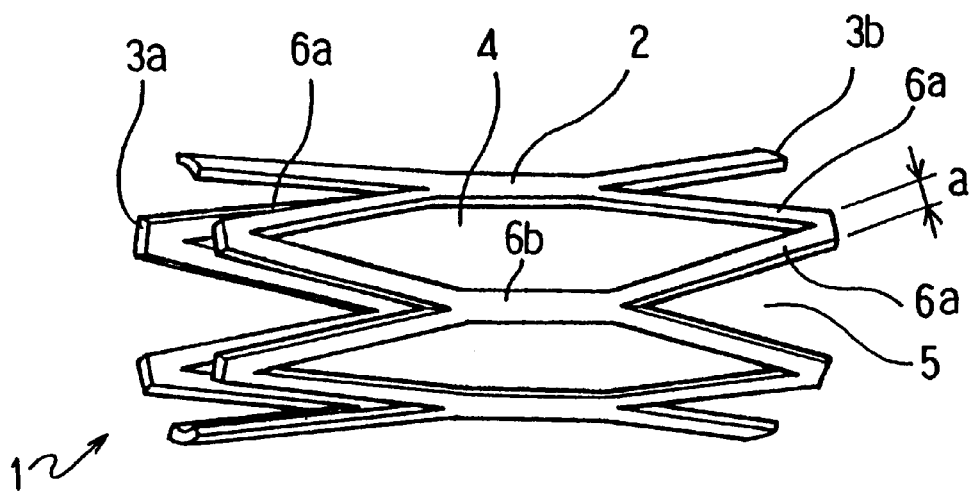
FIG. 1 is a perspective view of an embodiment of the stent of this invention.

The stent of this invention is described below using the embodiments shown in the drawings.

FIG. 1 is a perspective view of an embodiment of the stent of this invention.

The stent 1 of this invention is formed in a substantity circular cylinder of a super elastic metal that has a super high resilience both before and after the stent is put in the body. The stent 1 has a high deformability to deform in the direction to which the outside diameter becomes smaller when a pressure is applied by a frame structure with a plurality of notches and holes. Further, the stent 1 is formed as a single piece without an abrupt change in its physical property.

Specifically, the stent 1 has the shape as shown in FIG. 1.

The stent 1 of this embodiment comprises a cylindrical openwork frame 2, and holes 4 defined by side frame segments 6a and mele frame segments 6b and notches 5 defined by side frame segments 6a. The frame 2 has ends 3a and 3b. The entire frame 2 is made of a super elastic metal as a single piece in order to prevent an abrupt change in the physical property of the frame as at a part where separate pieces are connected.

The ends 3a, 3b are formed by a plurality of arcs which are disposed on a circle at intervals corresponding to about the same angles. That is, the ends of the frame 2 are of a complete, substantially correct circle if the notches 5 are not formed, and by forming the notches 5, the plurality of arcs disposed on the circle and separated by the notches are firmed. Further, the ends 3a and 3b are formed by the ends of the frame segments 6a. The frame segments 6a extend obliquely at a certain angle to the axis of the frame 2. The two side frame segments 6a branch and extend from both ends of each middle frame segment 6b, and the two side frame segments 6a extending from adjacent middle frame segments 6b converge together at the ends 3a and 3b to constitute an isoseles triangle as equal sides. The middle frame segments 6b extend approximately in parallel to the axis of the frame 2. In this embodiment, the middle frame segments 6b have a width twice or about twice that of the side frame segments 6a. The shape of the cross section of the frame segments 6a and 6b at right angles with the axis of the frame 2 is a in formed by longer and shorter arcs of the top (outer) and bottom (inner) sides and straight lines of the right and left sides. Further, the outside surface of the frame 2 is chamfered to prevent the edges from hurting the inside surface of a body wall.

Since the stent 1 of this embodiment has the notches 5 at the ends 3a and 3b, the local deformation of the end portions of the stent 1 are made possible, improving the capability of yielding to the deformation of the blood vessel in which the stent 1 is put. Further, since the ends 3a, 3b of stent 1 is formed by the ends of a plurality of frame segments 6a, the ends 3a, 3b have a sufficient strength not to readily collapse. Furthermore, the holes 4 defined by the side and middle frame segments 6a and 6b are formed between both ends. These holes 4 make easier the deformation of the middle part of the stent 1, especially in the direction to which the outside diameter decreases.

In this example, the holes 4 have the shape of a compressed hexagon, and the notches 5 have the shape of an isosceles trangle. The number of notches 5 formed at each end is six, and the notches have approximately the same shape. The number of the holes 4 formed in cylindrical wall of the stent 1 is also six, and the shapes of the holes are substantially the same. However, the number and shape of the notches and holes are not limited to those of this embodiment. The number of notches is preferably about 3 to 10, and that of the holes is also about 3 to 10. The outside diameter of the stent 1 is within the range of 2.0 to 30 mm, preferably 2.5 to 20 mm. The inside diameter is within the range of 1.4 to 29 mm, preforably 1.6 to 29.4 mm. The length is within the range of 10 to 150 mm, preferably 15 to 100 mm.

The super elastic metal for the stent 1 is preferably a super elastic alloy. A super elastic alloy here refers to an alloy which is generally called "a shape-memory alloy" and resumes its original shape after being deformed to such a degree that an ordinary metal undergoes permanent deformation at the body temperature (around 37° C.) at the highest. Preferable super elastic alloys are Ti—Ni alloy consisting essentially of 49 to 53 atom percent of Ni, Cu—Zn alloy consisting essentially of 38.5 to 41.5 wt % of Zn, Cu—Zn—X alloy containng 1 to 10 wt % of X (X=Be, Si, Sn, Al, or Ga), and Ni—Al alloy consisting essentially of 36 to 38 atom percent of Al Ti—Ni alloy is especially preferable. The mechanical property of Ti—Ni alloy can be changed as desired by replacing part of Ti—Ni alloy with 0.01 to 30.0 atom percent of X (X=Cu, Pd, or Zr) or selecting the reduction ratio of cold working and/or the conditions of the final heat treatment.

The buckling strength yelding stress when a load is increased) of the super elastic alloy used is 5 to 200 kg/mm$^2$ (22° C.), preferably 8 to 150 kg/mm$^2$, and the recovery stress (yielding stress when a load is decreased) is 3 to 180 kg/mm$^2$ (22° C.), preferably 5 to 130 kg/mm$^2$.

The stent 1 is made, for example, by forming a pipe of a super elastic metal and then removing the parts of the pipe at which the notches or holes are to be formed, and hence is a single piece without an abrupt change in the physical property of the stent. If there is the part at which the physical property changes abruptly, that part deirims diffirently from the other parts, distorting the shape of the entire stent unnaturally. The distorted shape can cause an unnatural blood flow which can cause a constriction again. There is also the possibility of breaking from that part because of a stress concentration. However, since the stent of this invention is made as a single piece within which an abrupt change in the physical property does not occur, it has no problems as described above.

The pipe of a super elastic metal can be prepared by melting a super elastic alloy such as Ti—Ni alloy in an inert gas or vacuum to cast an ingot, polishing the ingot mechanically, hot-pressing and extruding the ingot into a large-diameter pipe, drawing the pipe through dies and heat-treating it repeatedly to make the pipe thinner in wall thickness and smaller in outside diameter down to the predetermined wall thickness and outside diameter, and finally polishing the surface of the pipe physically or chemically.

The notches and holes can be formed in the pipe by laser (YAG laser, for example), electrical discharge, chemical etching, mechanical cutting, or combined use of them.

Figure 2:
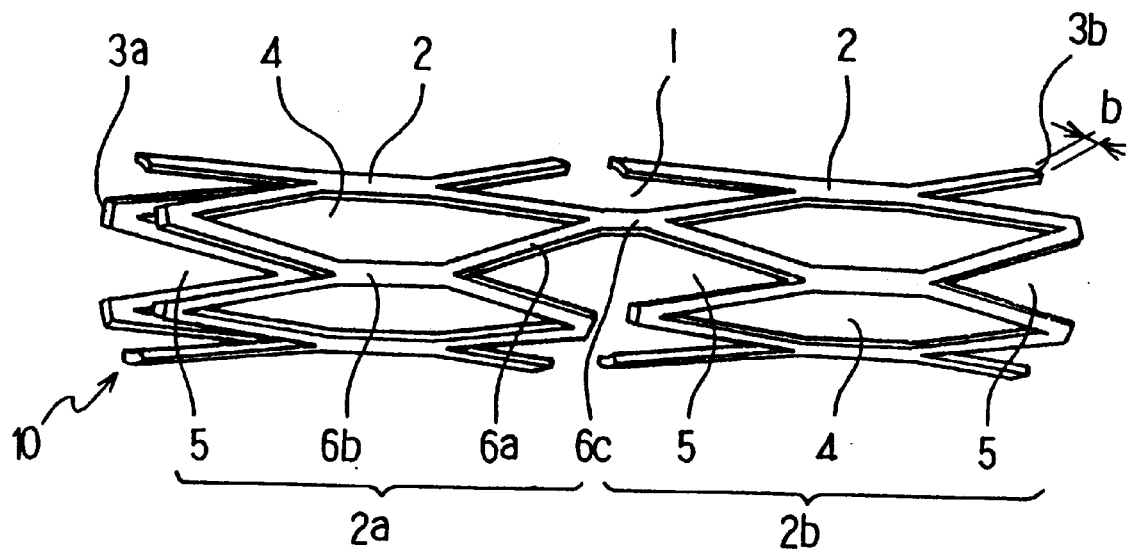
FIG. 2 is a perspective view of another embodiment of the stent of this invention.

Next, the stent of the embodiment shown in FIG. 2 is described below.

The stent 10 of this embodiment is the same as the one shown in FIG. 1 in the basic structure.

This stent 10 is used for a comparatively long stenosed part or stenosed part in a bent or wound blood vessel. This stent has a shape such that two stents, each being the one as shown in FIG. 1, are connected by a frame segment 6c. This stent 10 is also made as a single piece without an abrupt change in the physical property within it as the one describe above.

Specifically, one of the ends of the side frame segments 6a of one frame 2a and that of another frame 2b are connected by a intermediate frame segment 6c. The other ends of the side fame segments 6a are left free. Thus connected by only one frame segment, the stent 10 can deform easily up to a large extent between the frames 2a and 2b, and is effective for ameliorating a comparatively long stenosed part or stenosed part in a bent or wound blood vessel Further, the stent 10 can produce the desired effect by itself, eliminating the need of using two or more stents.

Figure 3:
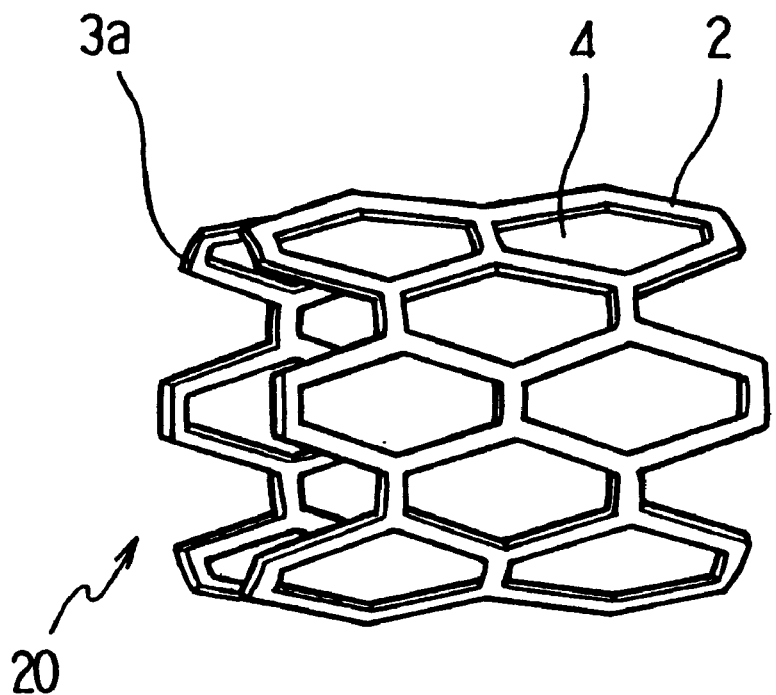
FIG. 3 is a perspective view of another embodiment of the stent of this invention.
Figure 4:
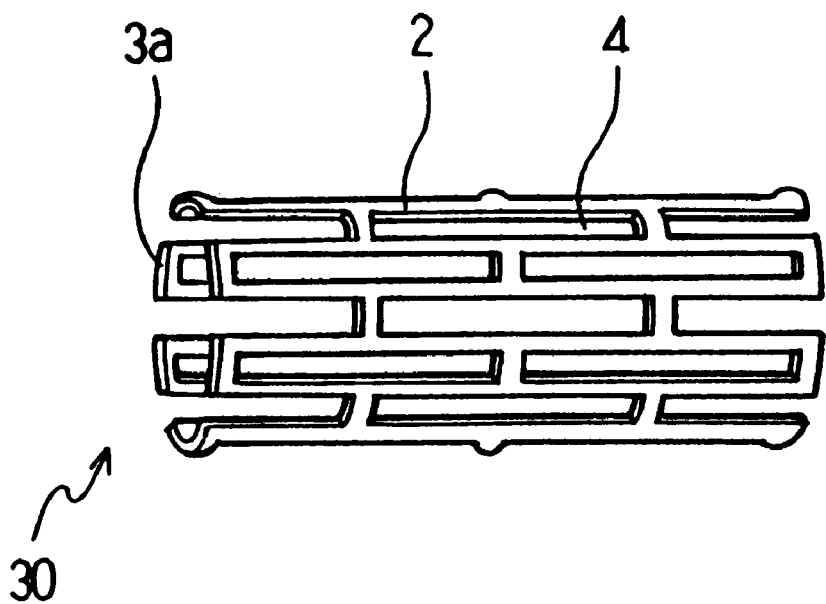
FIG. 4 is a perspective view of another embodiment of the stent of this invention.

The shape of the stent of this invention is not limited to those of the stents shown in FIGS. 1 and 2, but may be other shapes, such as the stent 30 shown in FIG. 3 which has trapezoidal notches at both ends and hexagonal holes disposed as the cells of a honeycomb in the middle portion, and the stent 40 shown in FIG. 4 which has rectangular notches at both ends and rectangular holes (twice longer than the notches) in the middle portion With the stents of the above embodiments of FIGS. 1 to 4, the difference in the shape and dimensions of the two states—the expanded state after the stents are put in the body (released from the pressing force) and the compressed state when they are put in the body (subjected to a pressing force)—is very small and therefore the movement of the ends in the direction of the axis caused by the change of the shape is also very small. As the result, the possibility that they can hurt the inside surface of a body wall when they expand to their original shape is substantially eliminated.

The stent of this invention may be made of a super elastic metal alone, or the outside surface, inside surface or both of them may be coated with an appropriate biocompatible material. For the biocompatible material, biologically compatible synthetic resins and metals may be used.

For the method of plating the surface of the stent with an inert metal, gold plate by electmplating, stainless steel plate by evaporation, and silicon-carbide, titanium nitride or gold plate by sputtering can be used.

For the synthetic rosins a resin chosen from thermoplastic and thermosetting resins such as polyolefin (polyethylene, polypropylene, ethylene-propylene copolymer, for example), poly(vinyl chloride), ethylene-vinyl acetate copolymer, polyamide elastomer, polyurethane, polyester, fluororesin, and silicone rubber can be used Of these resins, polyolefin polyamide elastomer, polyester, polyurethane, and biodegradable resins (polylactic acid, polyglycol acid, and copolymer of them, for example) are preferable. It is preferable that the coating of the synthetic resin is suffice ntly flexible not to hinder the frame from bending. The thickness of the synthetic resin coating 5 is preferably within the range of 5 to 300 $\mu$m, preferably 10 to 200 $\mu$m.

For the method of coating the surface of the stent thin with a synthetic resin, immersion coating that immerses the frame into a molten or dissolved synthetic resin and chemical evaporation that forms a coat over the surface of the frame by polymerizing monomers on the surface can be used. When an extremely thin resin coat is required, immersion coating using a dilute solution and chemical evaporation are preferable.

Further, to increase the biocompatibility of the stent, a coat of an anti-thrombogenic material may be formed, or an anti-thrombogenic material may be fixed. For the anti-thrombogenic material various known reams may be used singly or in a mixture. For example, polyhydroxyethyl-methacrylate and a copolymer of hydroxyethylmethacrylate and styrene (HEMA-St-HEMA block copolymer, for example) are preferable.

Next, the method for manufacturing the stent of this invention is described below.

The method includes at least the process which prepares a super elastic metal pipe with an appropriate outside diameter for the part of the body in which the stent is put and the process that makes notches and holes in the prepared pipe.

The pipe of a super elastic metal can be prepared by melting (compounding) a super elastic alloy such as Ti—Ni alloy in an inert gas or vacuum to cast an ingot, polishing the ingot mechanically, hot-pressing and extruding the ingot into a large iameter pipe, drawing through dies and heat-treating the pipe repeatedly to make the wall thickess of the pipe thinner and the outside diameter smaller down to the predetermined dimensions, and finally polishing the surface of the pipe physically or chemically.

The process of making notches and holes in the pipe can be performed by laser shaping (YAG laser, for example), electrical discharge shaping, machining such as grinding, chemical etching, or a combination of them.

Since the stents of these embodiments are made by working a pipe as described above, the outside diameter of the pipe becomes the outside diameter of the stent as it is, and consequently the precision of the dimension of the finished product is very high Therefore, these rents reliably resume the original shape in the stenosed part in which they are put and perform the function of ameliorating the stenosed part Further, since the stents of these embodiments are of a single piece with no abrupt change in the physical property within the stent, they do not have the problems of breaking from a stress concentration or cause an unnatural blood flow by an abnormal deformation.

More specifically, in the process of making notches and holes in a super elastic metal pipe, first the parts of the pipe at which notches or holes are to be made are removed by melting them by electrical discharge, and the pipe is thereby formed into a frame of almost the shape of the finished stent (first process).

Next, the frame is subjected to the churning process which removes edges and burrs of the frame (second process). This chamfering is permitted, for example, by shotblast using a fine hard abrasive.

The chamfered frame is then subjected to the chemical etching for removing the thermally denaturalize,ed parts around the notches and holes (third process: chemical etching). This etching is performed by immersing the frame in an etching liquid, for example, a mixture of fluoric acid and nitric acid with a little amount of hydrogen peroxide added. The removal of edges and burrs may be accomplished by chemical etching simultaneously with the removal of the thermally denaturalized parts In that case, shotblasting can be omitted.

The above first process of the process of making notches and holes in a super elastic metal pipe can also be performed by laser shaping (YAG laser, for example). Laser shaping removes the parts of the pipe at which notches and holes are to be made by melting them by laser light and forms a frame of almost the shape of the finished stent in the same manner as electric-discharge shaping.

This process can also be preformed by the photo-abrication technique in the following manner.

First, the inside and outside surfaces of the pipe are degreased and cleansed. This degreasing and cleansing are performed by immersing the pipe in an aqueous solution of a surface-active agent, RO water, or an organic solvent for cleansing such as hexane. After the pipe is dried, a photoresist is applied to the outside and inside surfaces of the pipe. The photoresist may be of either positive or negative type, uv resist, electron beam resist, or X-ray resist may also be used. The thickness of the photoresist coating is preferably within the range of 0.5 to 4 $\mu$m. Then, the photoresit coating is heat-treated at a temperature of 80 to 90° C. (pre-baking) to increase the adhesion of the photoresist coating to the pipe.

Next, a masking film with the patterns corresponding to the shapes of the notches and holes to be made is wound on the outside surface of the pipe and put into tight contact with the surface of the pipe by suction (the film used is different according to the type of the photoresist). The pipe is then subjected to the exposing process. The exposing is performed by using an extra-high voltage mercury-arc lamp. It is preferable to turn the pipe so that the entire surface is uniformly exposed to light. Next, the pipe is subjected to the developing treatment. The developing is performed by immersing the pipe in a photoresist developing reagent. The pipe is then subjected to the post-baking treatment which heats the photoresist to a temperature form 120 to 145° C. This completes the masking process.

By this masking process, the parts of the outside surface of the pipe at which notches or holes are to be made are exposed, while the other part of the outside surface and the entire inside surface of the pipe are covered with the hardened photoresist. This pipe is then immersed in an etching liquid. Those exposed parts of the pipe are put in contact with the etching liquid and dissolved by the action of the etching liquid. Those exposed parts of the pipe are put in contact with the etching liquid and dissolved by the action of the etching liquid, while the part of the pipe covered with the hardened photoresist does contact with the etching liquid and is not dissolved. By this etching process, a frame (unfinished stent) of almost the shape of the finished stent is made.

Next, the hardened photoresist remaining on the surface of the unfinished stent is removed This process is performed by immersing the frame in a solution that dissolves hardened photoresist.

Next, the frame is subjected to shotblast to round the edges and remove the burrs as described above. This unfinished stent is then immersed in the etching solution for a surface treatment. As the result, the stent of these embodiment is obtained.

This stent may be further subjected to a coating process for plating a metal or forming a resin coat as necessary.

The indwelling stent of this invention, being made as described above, is easy to put into a stenosed part. It can reliably dilate a stenosed part and maintain the dilated state, as an elect of using a super elastic metal that exhibits a super high resilience both belbre and after the stent is put in the body.

Further, the stent of this invention is of a substantially circular cylinder and has a plurality of notches and holes made in the cylinder to facilitate the deformation, the difference in the shape and dimensions of the two states of the stent—the expanded state after the stent is put in the body (released from the pressing force) and the compressed state when it is put in (subjected to the pressing force)—is small, hence the move of the ends in the direction of the axis caused by the change of the shape is also very small. As the result, the possibility that the stent can hurt the inside surface of a body wall when it expands to its original shape is substantially eliminated.

Further, the length of the stent viewed by means of X rays when the stent is put in substantially does not change after being put in. Therefore, the stent can be easily and accurately put in the intended stenosed part.

Further, the stent does not have the part at which the physical property changes abruptly. Therefore, the possibility of breaking at the part because of a concentration of stress is substantially eliminated if the stent is indwelled in a long time. There is also little possibility that the stent obstructs a smooth blood flow because of an abnormal deformations at the part, if used as a stent for dilating a blood vessel.

By the method for manufacturing the stent of this invention as described above, the stent with these advantages can be easily and effectively manufactured. Further, the stent can be made precisely in the dimensions, especially the outside diameter, suited to the part of the body in which the stent is put. Therefore, the stent can reliably resumes the shape in which it is manufactured and ameliorate a stenosed part when it is put in the body.

Next, another embodiment of the stent of this invention is described below with reference to the drawings.

Figure 5:
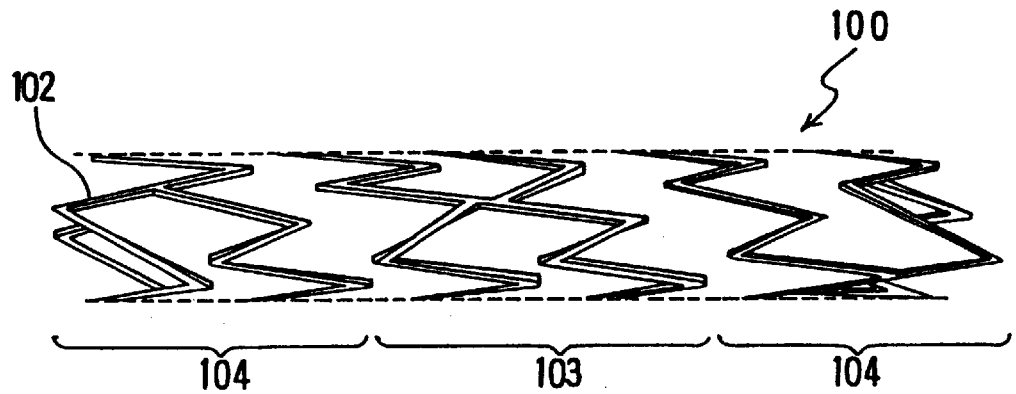
FIG. 5 is a perspective view of an embodiment of the indwelling stent of this invention.
Figure 6:
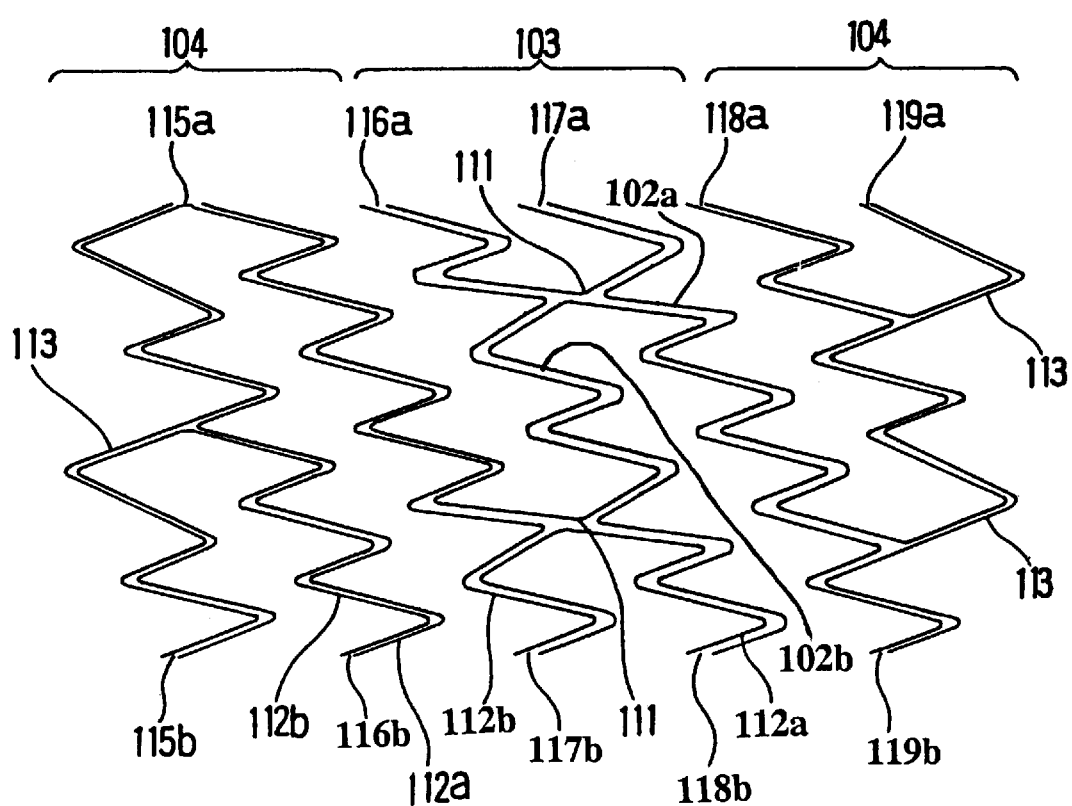
FIG. 6 is a developed view of the indwelling stent shown in FIG. 5.

FIG. 5 is a perspective view of en embodiment of the indwelling stent of this invention. FIG. 6 is a developed view of the stent shown in FIG. 5.

The indwelling stent 100 of this embodiment is made of wires 102 in the shape of a substantially circular cylinder. This stent is compressed to a smaller-diameter when it is put into the body, and is released from the load to expand to the shape before it is compressed after being put in the body. The wires 102 are formed relatively large in cross section in the middle portion 103, and relatively small in cross section in both end portions 104.

The indwelling stent of this embodiment is a so called self-expandable stent that is made of wire of an elastic material in a substantially circular cylinder. The wires in the middle portion of the stent are formed relatively large in cross section, and therefore the middle portion of the stent has a enough rigidity to dilate a stenosed part and maintain the openness. The wires in both end portions of the stent, on the other hand, are ibrmed relatively small in cross section, and hence the end portions of the stent are flexible and deforms along the bends in the stenosed part and its vicinity. Therefore, the possibility that the stent stimulates the endothelial cells to invoke a hyperpi of the cells which can cause a steno again is very small Further, since both end portions of the stent are flexible, the insertion of the stent into a stenosed part is made easier, and the stent stably remains in the stenosed part without shifting out of place.

The stent 100 of this embodiment is formed in a substantially circular cylinder having an outside diameter within the range of 2.0 to 30 mm, preferably 2.5 to 20 mm, an inside diameter within the range of 1.4 to 29 mm, preferably 2.3 to 29.4 mm, and a length within the range of 10 to 150 mm, preferably 15 to 100 mm when not compressed, depending on the part of the body in which the stent is put. The stent is compressed to a smaller outside diameter when being put into a part of the body, and resumes the original shape after being put in and reload from the pressing force. FIG. 5 shows the state in which the original shape is resumed.

The stent 100 is made of wires 102. The wires 102 in the middle portion 103 are formed relatively large in cross section, and those in both end portions 104 are formed relatively narrow in cross section. It is preferable that the wires 102 in the middle portion 103 are formed wide and those in both end portions 104 are formed narrow. Since the stent 103 of this invention is thus made, the middle portion 103 has a relatively high rigidity enough to dilate a stenosed part and maintain the dilated state. On the other hand, both end portions 104 are flexible enough to deform along the bends in the stenosed part and its vicinity.

Therefore, the possibility that the ends of the stent stimulates the endothelial cells to start a hyperplasia which can cause another stenosis is very small. Further, the insertion of the stent into a stenosed part is made easier, and the stent stably remains in the stenosed part without shifting out of place.

The diameter of the wires in the middle portion of the stent is preferably within the range of 0.10 to 1.0 mm, and the diameter of the wires in both end portions is preferably within the range of 0.05 to 0.8 mm. Further, the ratio of the diameter of the wires in the middle portion to those of the wires in both end portions is preferably within the range of 3 to 1:1, preferably 2 to 1:1.

The cross-sectional area of the wires in the middle portion of the stent is preferably within the range of 0.01 to 1 mm$^2$, and the cross-sectional area of the wires in both end portions is preferably within the range of 0.0025 to 0.64 mm$^2$. Further, the ratio of the cross-sectional area of the wires in the middle portion to those of the wires in both end portions is preferably within the range of 9 to 1:1, preferably 4 to 1:1.

Figure 7:
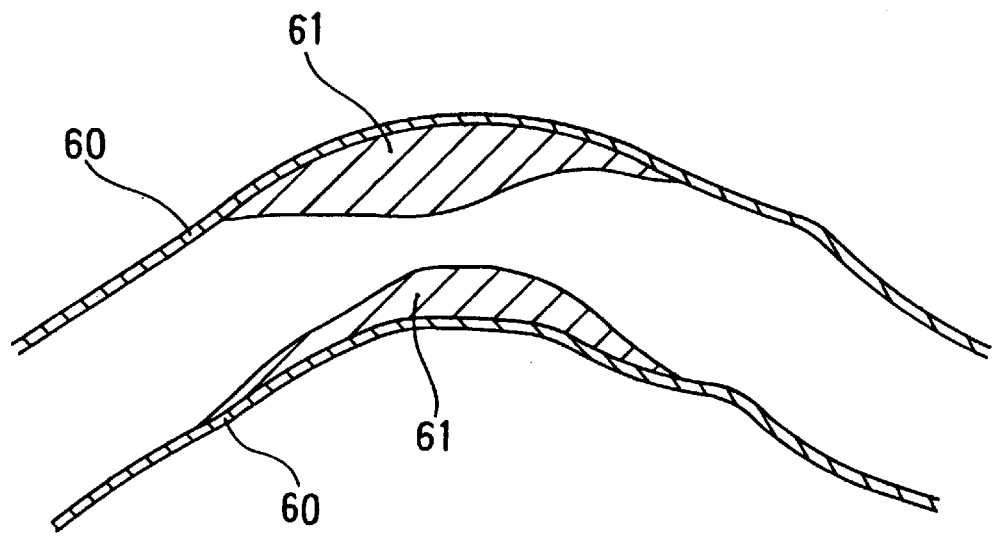
FIG. 7 is a sectional view which roughly illustrates the common state of a stenosed part in a vessel or hollow organ of the body.

It is preferable that the diameter (or crosssectional area) of the wires becomes gradually smaller form the middle portion 103 to both end portions 104, though the diameter of the wires may be constant in the middle portion 103 and in both end portions 104. The stent of this structure is suitable for the common stenosed parts as shown in FIG. 7.

Figure 8:
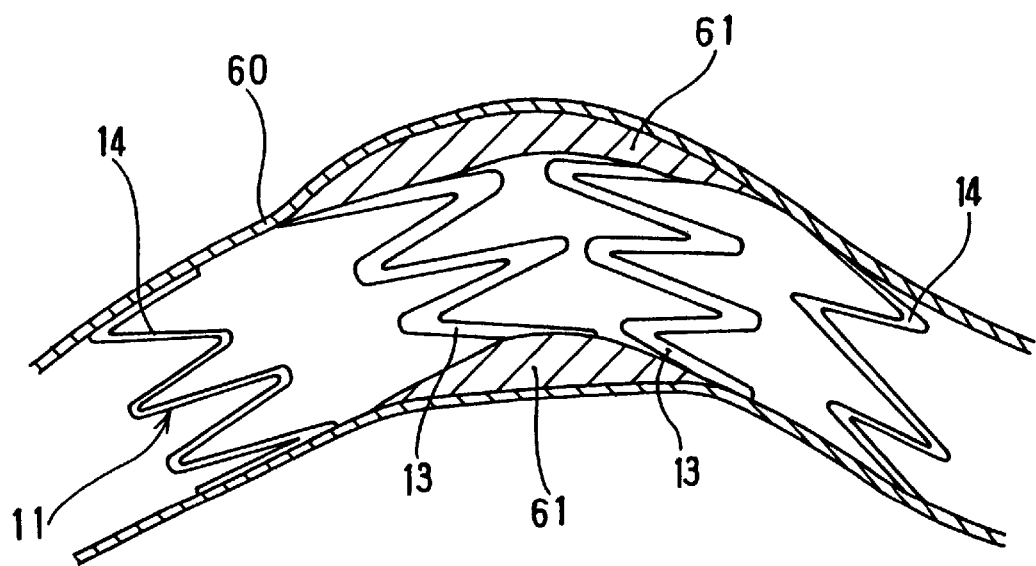
FIG. 8 illustrates the effect of an embodiment of the indwelling stent of this invention.

The stent 100 of this invention is made of zigzag wires 102 each extending helically as shown in FIG. 5. The stent can reliably expands to a larger diameter when resuming the original shape by virtue of the zigzag form of the wires. Further, the stent can bend along a stenosed part if the stenosed part is bent by virtue of the helical form of the wires as shown in FIG. 8. However, the stent of this invention must not necessarily be formed of helically wound wires, but may be formed of braided wires, frame with polygonal notches and holes, or knitted wires, for example, if the wires in both end portions 104 are formed thinner than those in the middle portion 103.

Specifilly, the wires 102 of this embodiment are formed into a zigzag consisting of repeated "<" shape as shown in FIG. 6 that is a developed view of the stent of FIG. 5. Further, each wire 102 is formed into a helix by making one segment 112b of the "<" shape longer than the other segment 112a. The short segment 112a is about 5 mm, and the long segment is about 8 mm.

Figure 9A:
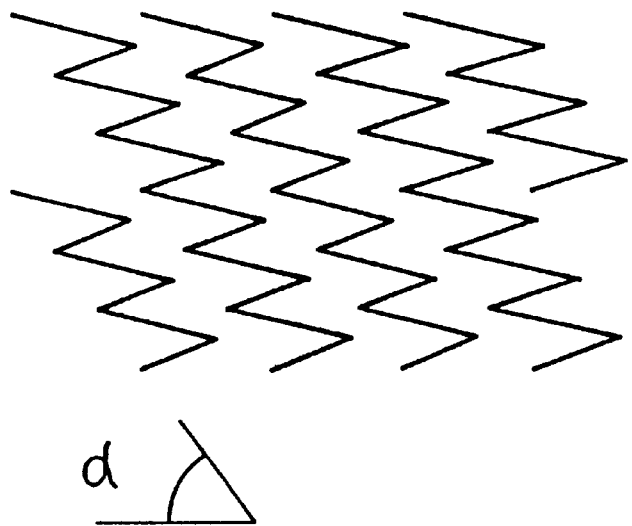
FIGS. 9(a) and 9(b) illustrate a part of an embodiment of the indwelling stent of this invention.
Figure 9B:
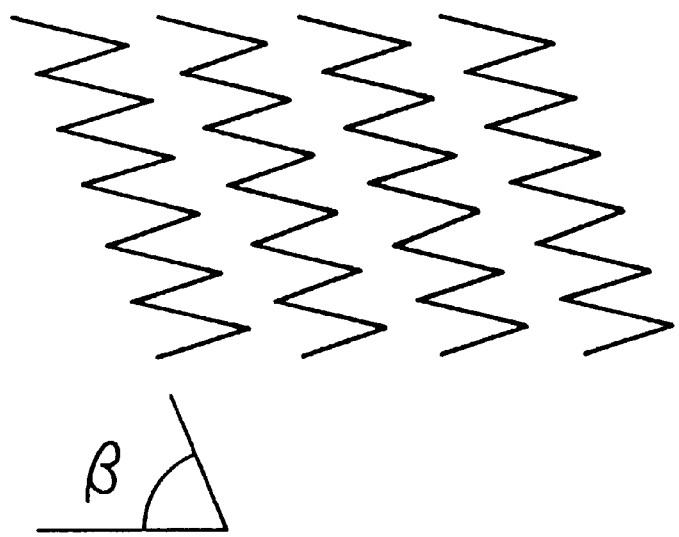

The helix structure of the stent 100 is formed of two wires disposed in parallel with each other as shown in FIG. 6. By thus forming the helix structure of two parallel wires, it becomes possible to make the angle α of the helix to the direction of the axis of the stent smaller than the corresponding angle β for the helix structure formed of a single wire (α<β) as shown in FIGS. 9 (a) and (b). As the result, the stent can be made more flexible. The number of wires disposed in parallel with each other may be greater than 2, for example, 3 or 4.

Since the two wires 102a and 102b in parallel with each other are wound helically, wire ends 115a and 115b, 116a and 116b, 117a and 117b, 118a and 118b, and 119a and 119b in FIG. 6 continue with each other.

Figure 24:
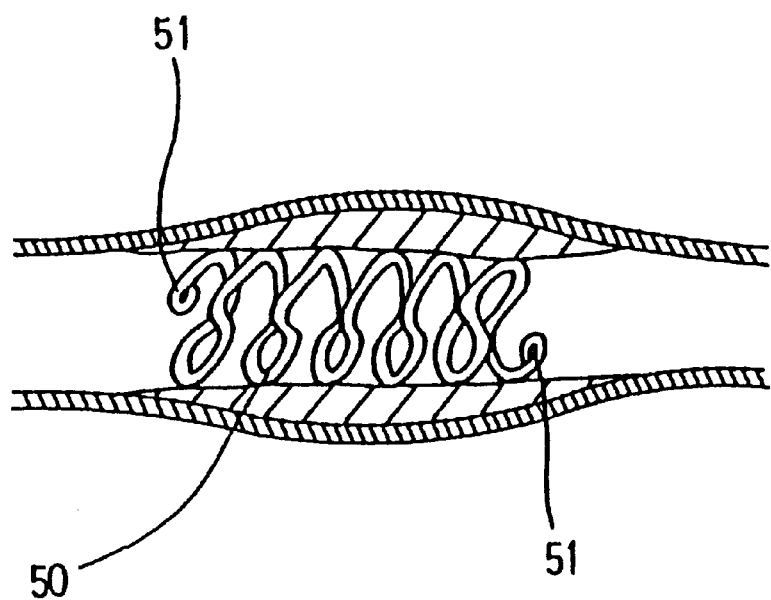
FIG. 24 illustrates the state in which the stent shown in FIG. 23 is used.
Figure 25:
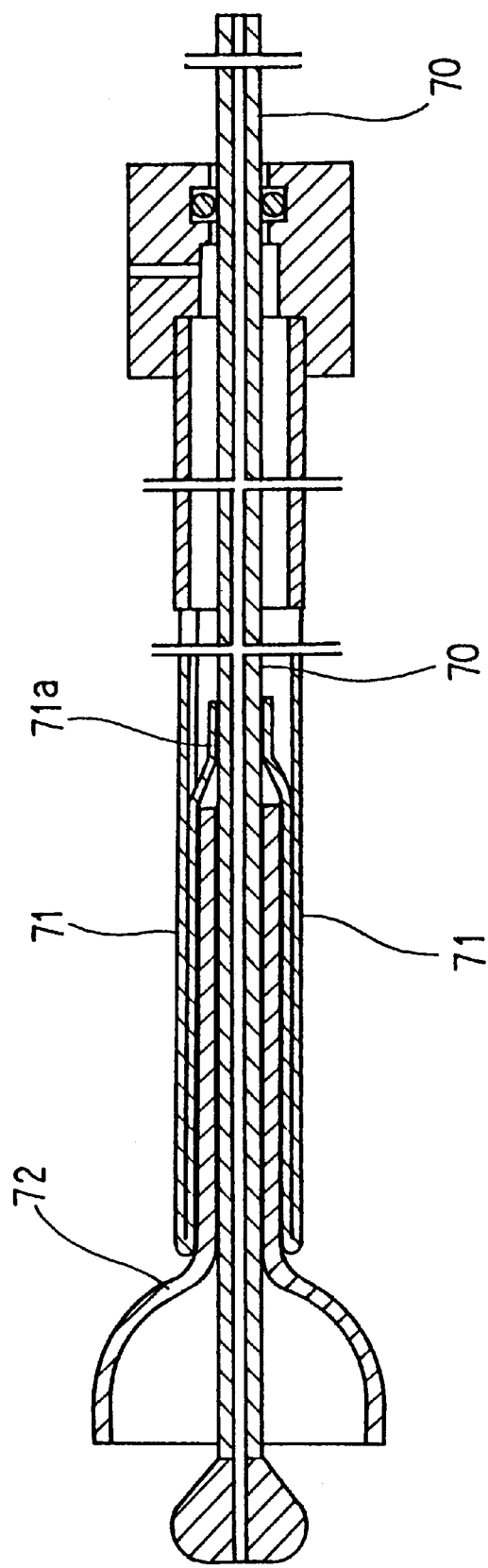
FIG. 25 is a sectional view of a conventional stenosis-treating device.

The two wires 102a and 102b are preferably connected with each other at least at two points, for example, at their ends. By connecting their ends so that those ends are not left as free ends, the possibility that free ends can hurt the inside surface of a body wall is eliminated, and special processes such as rounding free ends as required for the wires shown m FIG. 24 become unnecessary; In this embodiment, the end of each wire is connected with the other wire via a connecting segment as shown in FIG. 6.

Further, it is preferable that the two wires 102a and 102b are connected with each other in the middle portion 103. In this embodiment, the two wires 102a and 102b have junction points 111 in the middle portion 103. By making such junction points 111, the capability of the stent of dilating a stenosed part and maintaining the dilated state can be improved, though the two wires may be connected at both ends only.

The material of the wires 102 is preferably a super elastic metal, though stainless steel wires may also be used of the super elastic metals, a super elastic alloy is preferable. A super elastic alloy here refers to an alloy which is generally called "a shape-memory alloy" and resumes its original shape after being deformed to such a degree that an ordinary metal undergoes permanent deformation at the body temperature (around 37° C.) at the highest. Preferable super elastic alloys include Ti—Ni alloy consisting essentially of 49 to 53 atom percent of Ni, Cu—Zn alloy consisting essentially of 38.5 to 41.5 wt % of Zn, Cu—Zn—X alloy containing 1 to 10 wt % of X (X=Be, Si, Sn, Al, or Ga), and Ni—Al alloy consisting essentially of 36 to 38 atom percent of Al.

Ti—Ni alloy is especially preferable. The mechanical property of Ti—Ni alloy can be changed as desired by replacing part of Ti—Ni alloy with 0.01 to 10.0 atom percent of X (X=Co, Fe, Mn, Cr, V, AL Nb, W, B), replacing part of Ti—Ni alloy with 0.01 to 30.0 atom percent of X(X=Cu, Pd, or Zr), or selecting the reduction ratio of cold working and/or the conditions of the final heat treatment.

The buckling strength (yielding stress when a load is increased) of the super elastic alloy used is 5 to 200 kg/mm$^2$ (22° C.), preferably 8 to 150 kg/mm$^2$, and the recovery stress (yielding stress when a load is decreased) is 3 to 180 kg/mm$^2$ (22° C.), preferably 5 to 130 kg/mm$^2$.

The stent 100 is preferably made of a super elastic metal pipe as a single piece. Specifically, the stent 100 can be made by removing (cutting or melting, for example) the parts of a super elastic metal pipe other than those parts which become the wire structure. The stent 100 made by this method becomes a single piece without an abrupt change in the physical property within it. If there is the part at which the physical property changes abruptly, that part deforms differently from the other parts, distorting the shape of the entire stent unnaturally. The distorted shape can cause an unnatural blood flow which can cause a constriction again. There is also the possibility of breaking from that part because of a stress concentration.

A super elastic metal pipe used for making the stent 100 can be prepared by melting (compounding) a super elastic alloy such as Ti—Ni alloy in an inert gas or vacuum to cast an ingot, polishing the ingot mechanical; hot-pressing and e during the ingot into a large-diameter pipe, drawing through dies and heat-treating the pipe repeatedly to make the wall thickness of the pipe thinner and the outside diameter smaller down to the predetermined theses and diameter, and finally polishing the surface of the pipe physically or chemically.

The shaping of the super elastic metal pipe prepared can be performed by laser shaping (YAG laser, for example), electrical discharge shaping, chemical etching, mechanical cutting, or a combination of them.

The difference in the shape and dimensions of the two states of this stent —the expanded state after the stent is put in the body (released from the pressing force) and the compressed state when it is put in the body (subjected to a compressed force)—is very small, and the move of the ends in the direction of the axis caused by the change of the shape is also very small. Therefore, the possibility that the stent can hurt the inside surface of a body wall when it expands to its original shape is substantially eliminated.

The entire outside surface of the stent is preferably chained to prevent the edges of the stent of hurting the inside surface from the body.

The synthetic resin for coating the stent can be chosen from thermoplastic and thermosetting resins such as polyolefin (polyethylene, polypropylene, ethylene-propylene copolymer, for example), poly(vinyl chloride), ethylene-vinyl acetate copolymer, polyamide elastomer, polyurethane, polyester, fluororesin, and silecone rubber. Polyolefin polyamide elastomer, polyester and polyurethane, and biodegradable resins (polylactic acid, polyglyonl acid, and copolymer of them, for example) are preferable. It is preferable that the coating of the synthetic resin is sufficiently flexible not to hinder the wire frame from bending. The thickness of the synthetic resin coating 5 is preferably within the range of 5 to 300 μm, preferably 10 to 200 μm.

For the method of coating the surface of the stent thin with a synthetic resin, immersion coating that immerses the wire frame into a molten or dissolved synthetic resin and chemical evaporation that ibrms a coat over the surface of the wire frame by polymerizing monomers on the surface can be used. When an extremely thin resin coat is required, immersion coating using a dilute solution and chemical evaporation are preferable.

Further, to increase the biocompatibility of the stent, a coat of an anti-thrombogenic material may be formed, or the same material may be fixed. For the anti-thrombogenic material, various known resins may be used singly or in a mixture. For example, polyhydroxyethylmethacrylate and copolymer of hydlroxyethylmethacrylate and styrene HMA-St-HEMA block copolymer, for example) are preferable.

For the biocompatible metal, gold, silver, platinum, and titan can be used.

For the method of plating the surface of the wires 102 with a biocompatible metal, gold plate by electroplating, stainless steel plate by evaporation, and silicon-carbide, titanium nitride or gold plate by sputtering can be used.

Next, the method for manufacturing the stent of this embodiment is decide below.

The method includes at least the process which prepares a super elastic metal pipe with an appropriate outside diameter for the part of the body in which the stent is put and the process which removes the parts of the prepared pipe other than the part which becomes the wire frame.

The pipe of a super elastic metal can be prepared by melting (compounding) a super elastic alloy such as Ti—Ni alloy in an inert gas or vacuum to cast an ingot, polishing the ingot mechanically, hot-pressing and extruding the ingot into a large-diameter pipe, drawing through dies and heat-treating the pipe repeatedly to make the wall thickness of the pipe thinner and the outside diameter smaller down to the predetermine thickness and diameter, and finally polishing the surface of chemically the pipe physically.

The process of removing the unnecessary parts of the super elastic metal pipe can be performed by layer shaping (YAG laser, for example), electrical discharge shaping, grinding or cutting, or chemical etching or a combination of them.

Since the stent of this embodiment is made by working a pipe as described above, the outside diameter of the pipe becomes the outside diameter of the stent as it is, and consequently the precision of the dimension of the finished product is very high. Therefore, this stent reliably resumes the original shape in the stenosed part in which it is put and performs the function of ameliorating the stenosed part. Further, since the stent of this embodiment is of a single piece with no abrupt change in the physical property within it, it does not have the problems of breaking from a stress concentration or causing an unnatural blood flow by an abnormal deformation. Moreover, neither welding nor soldering, the work condition of which is difficult to control, is required.

Specifically, in the process of removing the unnecessary parts of a super elastic metal pipe, first the parts of the pipe other than the part which becomes the wire frame are removed by melting them by electrical discharge, and the pipe is formed into almost the shape of the finished stent (first process). In this first process, the wire frame is formed so that the wires in the middle portion are thick (large in cross-sectional area) and the wires in both end portions are thin (small in cross-sectional area). The wire frame may also be formed so that the wires in the middle portion are wide and the wires in both end portions are narrow.

Next, the wire frame (unfinished stent) is subjected to the chamfering process which removes edges and burrs of the wire frame (second process). This chamfering is performed, for example, by shotblast using a fine hard abrasive.

The wire frame is then subjected to the chemical etching for removing the thermally denaturalized parts of the wire frame around the holes (third process: chemical etching). This etching is performed by immersing the shotblasted wire frame in an etching liquid, for example, a mixture of fluoric acid and nitric acid with a little amount of hydrogen peroxide added. The removal of edges and burrs may be performed simultaneously with the removal of the thermally denaturalired parts by chemical etching. In that case, the shotblast can be omitted.

When the stent of this embodiment is formed of Ni—Ti super elastic alloy, the wire frame may be made by first forming the wire frame of a uniform wire thickness and then subjecting it to the end-shaping process which makes the wires in both end portions thinner. This end-shaping process is performed by immersing the wires in both end portions in a processing solution (a mixture of fluoric acid and nitric acid prepared at a predetermined concentration). In this process, each end portion is separately processed. Further, the wires in both end portions can be made gradually thinner toward the ends by dipping each end portion in the processing solution and slowly pulling it out the solution. This method can be used for the stent of other structures, such as braided wires, frame with polygonal notches and holes, or knitted wires as described above.

The above first process of the wire-frame shaping process can also be performed by laser shaping (YAG laser, for example). laser shaping removes the unnecessary parts of the pipe by melting them by laser light and forms a frame of almost the shape of the finished stent in the same manner as electrical discharge shaping.

This can also be performed by the photo-fabrication process in the following manner.

First, the inside and outside surfaces of the pipe are degresed and cleansed. This degreasing and cleansing are performed by immersing the pipe in an aqueous solution of a surface-active agent, RO water, or an organic solvent used for cleansing such as hexane. After the pipe is dried, a photoresist is applied to the outside and inside surfaces of the pipe. The photoresist may be either positive or negative type. UV resist, electron beam resist, or X-ray resist may also be used. The thickness of the photoresist coating is preferably within the range of 0.5 to 4 μm. Then, the photoresist coating is heat-treated at a temperature of 80 to 90° C. (pre-baking) to increase the adhesion of the photoresist coating to the pipe.

Next, a masking film with the patterns corresponding to the shapes of the parts of the pipe to be removed is wound on the outside surface of the pipe and put into tight contact with the surface of the pipe by suction (the film is different according to the type of the photoresist). The pipe is then subjected to the exposing procss. The exposing is peribrned by using an extra-high voltage mercury-arc lamp. It is preferable to turn the pipe so that the entire surface is uniformly exposed to light. Next, the pipe is subjected to the developing treatment. The developing is performed by immersing the pipe in a photoresist developing reagent. The pipe is then subjected to the post-baking treatment which heats the photoresist to a temperature from 120 to 145° C. This completes the masking process.

By this masking process, the outside surface of the parts of the pipe to be removed are exposed, while the other part of the outside surface and the entire inside surface of the pipe are covered with the hardened photoresist. This pipe is then immersed in an etching liquid. Those exposed parts of the pipe are put in contact with the etching liquid and dissolved by the action of the etching liquid, while the part of the pipe covered with the hardened photoresist does contact with the etching liquid and is not dissolved. By this etching process, an wire frame (unfinished stent) of almost the shape of the finished stent is made.

Next, the hardened photoresist remaining on the surface of the unfinished stent is removed. This process is performed by immersing the wire fame in a solution that dissolves hardened photoresist.

Next, the wire frame is subjected to shotblast to round the edges and remove the burrs as described above. The wire frame is then immersed in an etching solution for a surface treatment. As the result, the stent of this embodiment is obtained.

This stent may be further subjected to a coating process for plating a metal or forming a resin coat as necessary.

Since the indwelling stent of this embodiment has the structure as described above, the middle portion of the stent has an enough rigidity to dilate a stenosed part and maintain the openness, and both end portions of the stent are flexible enough to deform along the bends in the stenosed part and its vicinity. Because of the flexibility of the end portions of the sent, the possibility that the ends of the stent stimulates the endothelial cells to a hyperplasia which can cause another stenosis is very small. Further, insertion of the stent into a stenosed part is easy. The stent stably remains in the stenosed part without shifting out of place.

Next, the stenosis-treating device of this invention is described below using the embodiment shown in the drawings.

Figure 10:
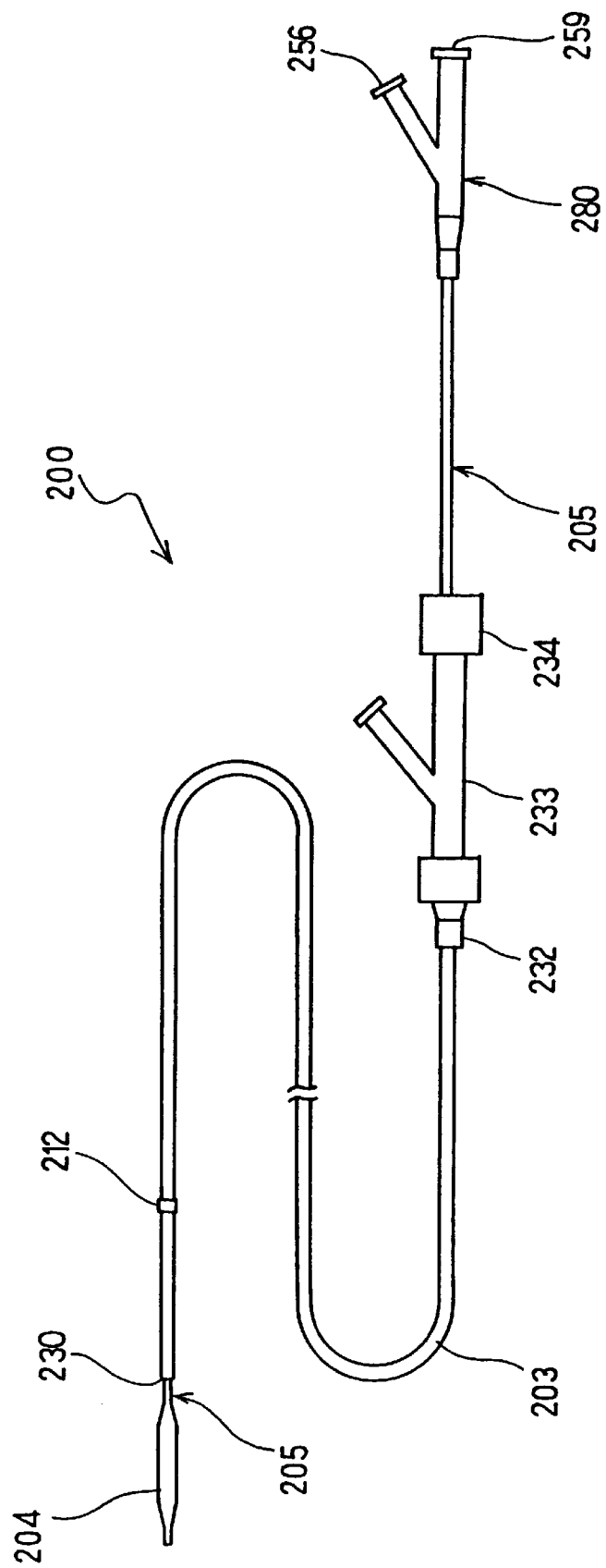
FIG. 10 is a front view of an embodiment of the stenosis-treating device of this invention.
Figure 11:
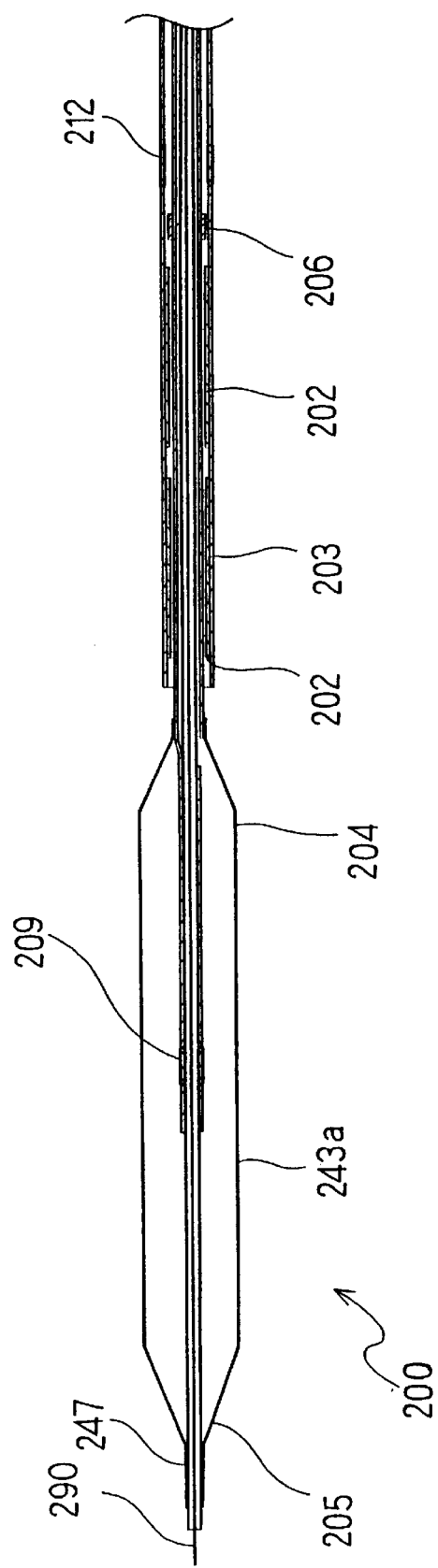
FIG. 11 is a diagrammatic view of the front end portion of the stenosis-treating device shown in FIG. 10.
Figure 12:
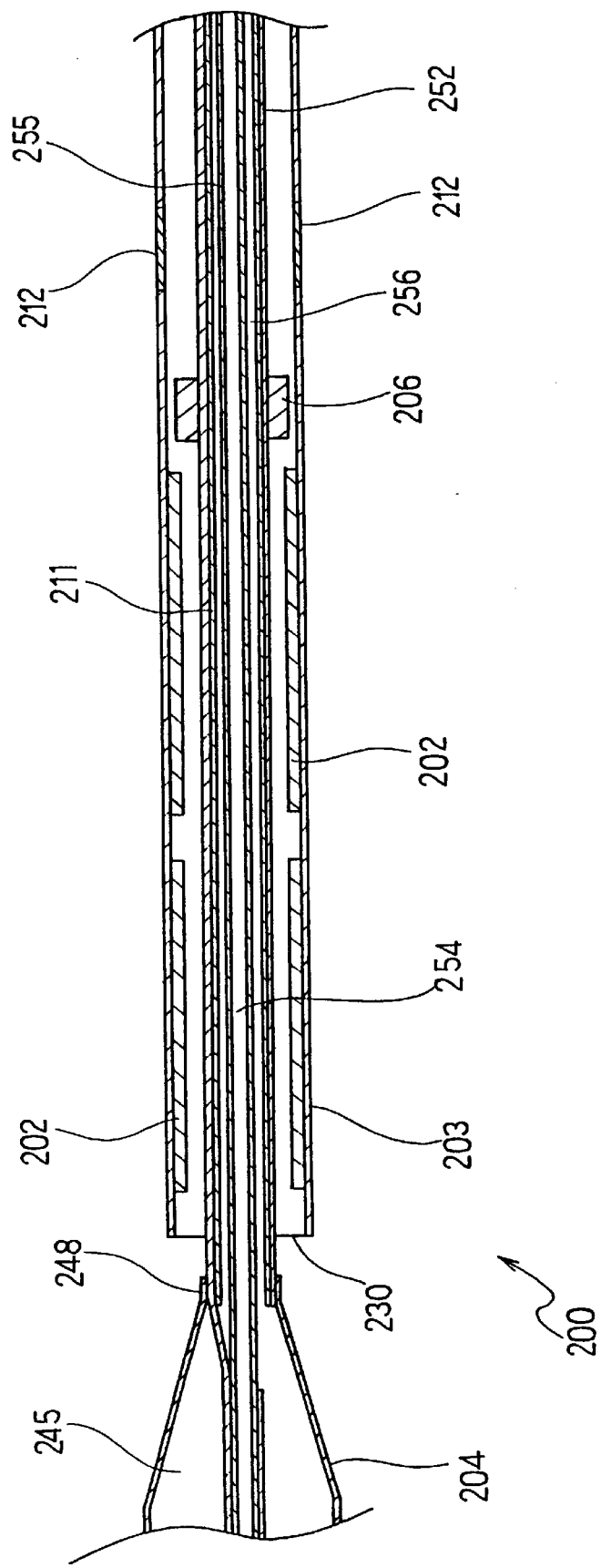
FIG. 12 is an enlarged sectional view of a part of the front end portion shown in FIG. 11.
Figure 13:
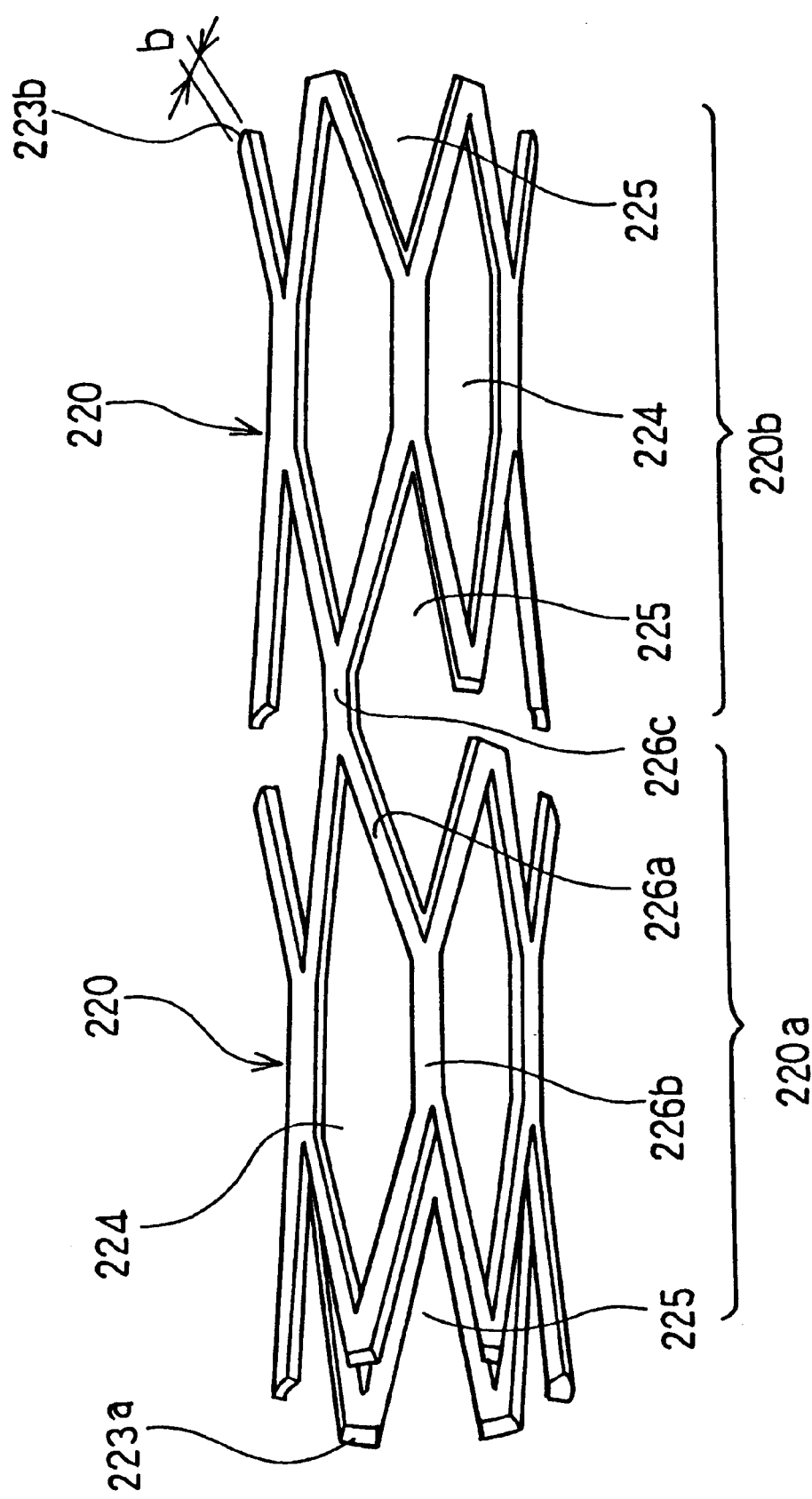
FIG. 13 is a perspective view of an embodiment of the indwelling stent used as a component of the stenosis-treating device of this invention.
Figure 14:
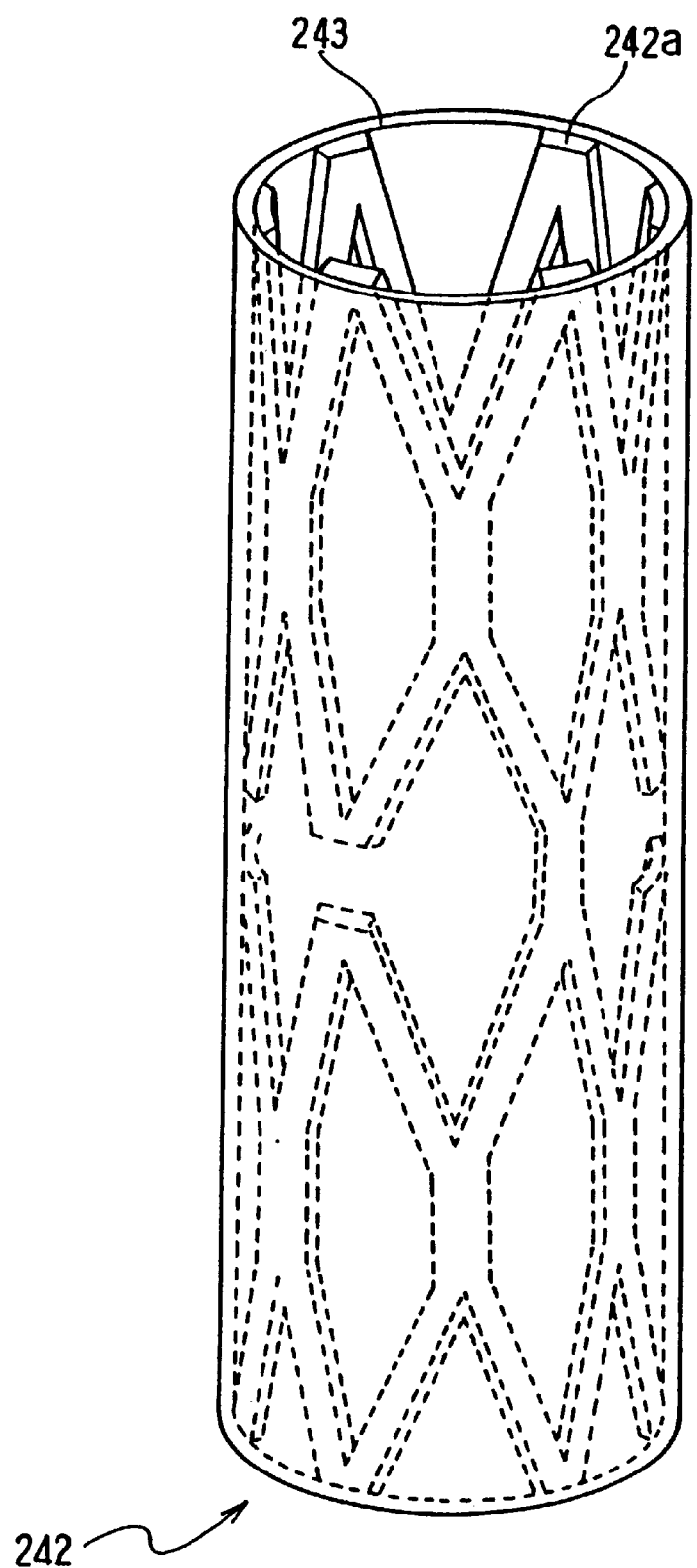
FIG. 14 is a perspective view of another embodiment of the indwelling stent used as a component of the stenosis-treating device of this invention.

FIG. 10 is a front view of an embodiment of stenosis-treating device of this invention. FIG. 11 is a diagrammatic sectional view of the front end portion of the stenosis-treating device of this invention. FIG. 12 is an enlarged view of a part of FIG. 11. FIG. 13 is a perspective view of an embodiment of the indwelling stent used 1hr the stenosis-treating device of this invention. FIG. 14 is a perspective view of another embodiment of the indwelling stent used for the stenosis treating device of this invention.

The stenosis-treating device 200 of this embodiment comprises an indwelling stent 202 in the shape of a substantially circular cylinder which is compressed to a smaller diameter when being put into the body and expands to the original shape after being put in the body, a sheath 203 which retains the stent 202 in the compressed state within it, and a balloon catheter 205 equipped with a balloon 204 at the portion which is passed through the stent 202 and the sheath 203 and extends beyond the front ends of the stent 202 and the sheath. The balloon catheter 205 has a projection 206 in the outside surface at the rear of the region at which the stent 202 is accommodated in the sheath 203 which comes into contact with the rear end of the stent 202 and stops the move of the stent 202 to let the stent 202 out of the sheath 203 when the sheath 203 is moved rearward.

Since the stenosis-treating device of this invention has a balloon catheter equipped with a dilatation balloon at the portion extending beyond the front ends of the sheath and the stent. It is possible that the stenosed part in which the stent is put is dilated a certain extent by inflating the balloon before the stent is put in. In addition, the stent can be held at a desired position in the stenosed part by inflating the balloon at the far side of the stenosed part, and therefore a self-expandable stent can be set at an accurate positioned, even in thin, sharply bent blood vessels such as coronary arteries.

Further, since the balloon catheter of the stenosis-treating device of this invention has a projection for stopping the move of the stent caused by the rearward move of the sheath, at the rear of the region at which the stent is accommodated in the sheath, the stent comes into contact with the projection and is retained in the stenosed part out of the sheath, then expands and dilates the stenosed part, and securely indwells in the stenosed part, when the sheath is pushed into the stenosed part together with the catheter and the sheath alone is moved rearward. The projection prevents to move the sent with the sheath after contacting to the stent.

The balloon catheter 205, which is passed through the stent 202 and the sheath 203 both of a substantially circular cylinder, comprises an inner tube 255 which has the first lumen 254 being open at the front end, an outer tube 252 which is disposed coaxially with the inner tube 255, has the front end receding a predetermined length from that of the inner tube 255, and forms the second lumen 256 between the inside surface and the outside surface of the inner tube 255, a balloon 204 which is contractable or foldable, has a front and rear ends, the rear end being bonded to the outer tube 252 and the front end being bonded to the inner tube 255, and communicates with the second lumen 256 near the rear end, and a branched hub 280 to which the rear ends of the inner tube 255 and the outer tube 252 are connected The branched hub 280 has the first opening 259 communicating with the first lumen 254 and the second opening 251 communicating with the second lumen 256 as shown in FIG. 16.

The inner tube 255 has the first lumen 254 with the open front end. The first lumen 254 is a lumen for passing a guide wire 290 through it and communicates with the first opening 259 made in a guide wire port 58 formed in the branched hub 280 (described later). The inner tube 255 is within the range of 0.40 to 2.50 mm, preferably 0.55 to 2.40 mm in outside diameter and within the range of 0.25 to 2.35 mm, preferably 0.30 to 1.80 mn in inside diameter. The inner tube 255 of this embodiment is formed to be 0.52 mm in outside diameter, 0.43 mm in inside diameter, and 0.045 mm in wall thickness.

The front end portion of the inner tube 255 preferably becomes gradually smaller in the outside diameter toward the front end This taper makes the insertion into a blood vessel easier. The inner tube 255 is passed through the inside of the outer tube 252 (described later), and the front end portion extends from the outer tube 252, as shown in FIG. 12. The second lumen 256 is formed between the outside surface of the inner tube 255 and the inside surface of the outer tube 252 and has an adequate crossectional area. This second lumen 256 communicates with the inside of the balloon 204 at the front end. The rear end of the second lumen 256 communicates with the second opening 251 made in the injection port 257 for injecting a liquid for inflating the balloon 204 (contrast medium for blood vessels, for example) as shown in FIG. 16.

An X-ray shadow producing part 209 is formed at the portion of the inner tube 255 inside the balloon 204 (described later). In this embodiment, the position at which the X-ray shadow producing part 209 is about the middle position on the ais of the balon 204. The X-ray shadow producing part 209 makes it possible to know the position of the balloon correctly by means of X rays and thereby makes the manipulation of the catheter easier. For the method for forming the X-ray shadow producing part, rings or coils of an appropriate X-ray opaque material (gold, platinum, platinum-iridium alloy, silver, stainless steel or an alloy of them) may be attached to the outside surface of the inner tube 255 by caulking, for example.

The outer tube 252 is within the range of 0.60 to 2.80 mm, preferably 0.80 to 2.60 mm in outside diameter and within the range of 0.50 to 2.70 mm, preferably 0.60 to 2.00 mm in inside diameter. The difference between the outside diameter of the inner tube 255 and the inside diameter of the outer tube 252 is within the range of 0.05 to 0.20 mm, preferably 0.1 to 1.20 mm. The outside tube 252 of this embodiment is formed to be 1.0 mm in outside diameter, 0.80 mm in inside diameter, and 0.1 mm in wall thickness.

For the material for the inner tube 255 and the outer tube 252, those materials with a certain degree of flexibility such as thermoplastic resins—polyolefins (polyethylene, polypropylene, ethylene-propylene copolymer, for example), poly(vinyl chloride), ethylene-vinyl acetate copolymer, polyamide elastomer, polyurethane, polyester, and fluororesin—and silicone rubber can be used. Of these resins, the thermoplastic resins are preferable, and polyolefins are more preferably.

The outside surface of the outer tube 252 may be coated with an appropriate biocompatible resin, especially an anti-thrombogenic resin For the anti-thrombogenic resin, polyhydroxyethyl-methacrylate and a copolymer of hydroxyethyl-methacrylate and styrene (HEMA-St-HEMA block copolymer, for example), for example are preferable.

In the balloon catheter 205 of this invention, the balloon 204 is disposed at the portion of the inner tube 252 extending beyond the front ends of the stent 202 and the sheath 203 as shown in FIG. 11. Since a balloon is disposed at this position, the stenosed part in which the stent is put is dilated a certain extent by inflating the balloon before the stent is put in. In addition, the stent can be held at a desired position in the stenosed part by inflating the balloon at the far side of the stenosed part, and therefore a self-expandable stent can be set at an accurate positioned, even in thin, sharply bent blood vessels as coronary arteries.

A balloon 204 is contractable or foldable, and is in close contact with or folded on the outside surface of the inner tube 255. The balloon has preferably a certain degree of shape-maintainabdity and a certain degree of elasticity. A high elasticit is preferable for fixing the catheter in a blood vessel (body cavity, etc.), and a high shape-maintainability is preferable for amelioration of stenosis. Therefore, it is preferable that the balloon has both of these properties at certain degrees.

When using a balloon 204 with a certain degree of shape-maintainability; it is preferable that the balloon has a substantially circular cylindrical portion 43a of substantially the same diameter so that it can dilate a stenosed part reliably and effectively. The substantially 1.50 to 35.00 mm, preferably, but may be a prism.

The front and rear end portions of the balloon 204 become gradually smaller toward their respective ends. The size of the balloon 204 is within the range of 1.50 to 35.00 mm, preferably 2.00 to 30.00 mm in the outer diameter and within the range of 10.00 to 80.00 mm, preferably 15.00 to 75.00 mm in the length for the circular cylindrical portion 43a when being inflated. Further, the balloon may also has a low shape-maintainability and a high elasticity.

The rear end portion 248 is bonded to the front end portion of the outer tube 252 in the liquid-tight Chion by an appropriate method such as an adhesive agent or fusing, and the front end portion 247 is bonded to the front end portion of the inner tube 255 in the liquid-tight fashion by the same method as shown in FIGS. 11 and 12.

The balloon 204 makes an expandable-and-contractable closed space 45 between its inside surface and the outside surface of the inner tube 255.

For the material for the balloon, those materials with a certain degree of flexibility, shape-maintainability, and elasticity are preferable. Thermoplastic resins include polyolefins (polyethylene, polypropylene, ethylenc-propylene copolymer, etc.), polyesters (poly(vinyl chloride), ethylene-vinyl acetate copolymer, bridged ethylene-vinyl acetate copolymer, polyurethane, polyethyleneterephthalate, etc.), and polyamide elastomers.

The materials with a high elasticity include silicone rubber, latex rubber, and the like.

It is preferable that the outside surface of the portion of the catheter which extends from the front of the sheath 203 and is not covered by the balloon has a high lubricity.

For this purpose, the aforementioned outside surface of the catheter may be covered with a hydrophilic polymer, such as poly(2-hydroxyethyl-methacrylate), polyhydroxyethylacrylate, hydroxypropylcellulose, methyl vinyl ether maleic anhydride copolymer, polyethylene glycol, polyacrylamide, or polyvinylpyrrolidone by coating or fixing. The inside surface of the inner tube may be covered with the same material by coating or fixing in order to increase the lubricity against the guide wire.

The branched hub 280 comprises an inner-tube hub 282 which is connected to the rear end of the inner tube 255 and has a guide-wire port 258 communicating the fist lumen 254 in the inner tube 255 with the first opening 259, and an outer-tube hub 283 which is connected to the rear end of the outer tube 252 and has an injection port 257 communicating the second lumen 256 between the inner and outer tubes with the second opening 251. The inner-tube hub 282 and the outer-tube hub 283 are connected together.

For the material for the branched hub 280, thermoplastic resins such as polycarbonate, polyamide, polysulfone, polyallylate, and methacrylate-butylene-styrene copolymer are preferably used. Instead of the branched hub 280, a tubular member which has a port portion with an opening in the rear end may be connected to each of the first and second lumens in the liquid-tight fashion.

Further, the balloon catheter 205 of this embodiment has a ridgity-imparting material 211 attached to the inside surface of the outer tube 252 as shown in FIG. 12. The rigidity-imparting material 211 prevents sharp bending and improves the torquetransmitting characteristic of the catheter. It is preferable that the rigidity-imparting material 211 is attached from the rear end of the outer tube 252 up to near the front end, that is, on almost entire length of the outer tube 252. The rigidity-imparting material 211 may also be attached on the outside surface of the inner tube 255.

The nrgidity-imparting material 211 is preferably a mesh. The mesh is preferably made of braid, for example, wire braid formed of wire of a metal such as a stainless steel elastic metal, super elastic metal and shape-memory alloy, 0.01 to 0.2 mm, preferably 0.03 to 0.1 mm in diameter. Instead of metal wire, fiber of a synthetic resin such as polyamide, polyester, and polypropylene may be used.

The balloon catheter 205 of the stenosis-treating device of this invention has a projection (rib) 206 on the outside surface at the rear of the region at which the stent 202 is accommodated in the sheath 203. The projection 206 comes into contact with the rear end of the stent 202 and lets the stent 202 out of the sheath 203 when the sheath 203 is moved rearward. In other words, this projection 206 performs the function of stopping the movement of the stent 202 being pulled by the sheath 203 when the sheath 203 is moved rearward.

Since the stenosis-treating device of this invention has the projection 206 in the outside surface of the baloon catheter, the stent is left in the stenosed part out of the sheath 203 by positioning the stent held within the sheath 203 in the stenosed part and pulling the sheath 203 rearward. Thus, by this simple structure, a self-expandable stent can be easily and accurately put in the desired stenosed part even in thin and sharply-bent blood vessels as coronary arteries.

The projection (ring rib) 206 of this embodiment is a ring which has an outside diameter smaller than the inside diameter of the sheath 203 and greater than the inside diameter of the stent 202 being compared to a smaller diameter. Therefore, the projection 206 does not hinder the move of the sheath 203 in the direction of the axis. Being in the shape of a ring, the projection 206 can reliably come into contact with the stent 202 and let the stent 202 out of the sheath 203.

The outside diameter of the projection 206 is within the range of 1.0 to 3.2 mm, preferably 1.1 to 3.0 mm. The ratio of the outside diameter of the projection 206 to the inside diameter of the sheath 203 is preferably within the range of 90/100 to 100/100. The outside diameter of the projection 206 of this embodiment is 1.40 mm. The inside diameter of the sheath 203 is 1.46 mm, and the wall thickness of the stent 202 is 0.1 mm as described above. Accordingly, the inside diameter of the stent 202 is 1.26 mm, the size such that the projection 206 of the outside diameter of 1.40 mm comes into contact with the stent 202 without fail.

However, the shape of the projection 206 is not limited to a ring, but may be any other shape that can reliably stop the move of the stent 202 being pulled by the rearward move of the sheath 203. For example, the projection 206 may be one or more than one separate radial projections in the outside surface of the balloon catheter. In other words, the projection 206 may be of any shape if the shape has the stopping portion(s) which comes into contact with the rear end of the stent compressed and can stop the stent by the stopping portion(s) without fail The projection 206 may be made separately from the outer tube or may be formed as an integrated part of the outer tube.

The projection 206 is preferably made of an X-ray shadow generating material (X-ray opaque material). By thus making the projection 206 of an X-ray opaque material, the position of the stent can be known easily and accurately by means of X rays. To make an X-ray opaque projection 206, a ring or coil of an appropriate X-ray opaque material (old, platinum, platinum-iridium alloy, silver, stainless steel or an alloy of them) can be attached to the outside surface of the outer tube 255 by caulking, for example.

The stent 202 used for this stenosis-treating device 200 is a so called self-expandable stent. Specifically, the stent 202 has the shape as shown in FIG. 13 (original shape resumed). The stent 202 of this embodiment comprises a circular-cylindrical frame consisting of two frame sections 220, and holes 224 defined by frame segments 226a and 226b which make the circular-cylindrical frame 220 and notches 225 defined by frame segments 226a. The frame 220 has two end 223a and 223b.

For the material for making the stent (frame), synthetic resins and metals can be used.

The synthetic resins are those which have both a certain degree of rigidity and elasticity. Biocompatible resins—specifically; polyolefin (polyethylene and polypropylene, etc.), fluororesin (PTFE, ETFE, etc.), and biodigestable materials such as polylactic acid, polyglycol acid, and copolymer of polylactic acid and polyglycol acid—are preferable.

The metals are preferably those with biocompatibility, such as sta steel, tantalum, and Ni—Ti alloy. Super elastic metals are especially preferable.

The stent 222 is made preferably as a single piece without an abrupt change in the physical property within it The stent is made, for example, by preparing a pipe of an outside diameter appropriate for the stenosed part in which the stent is used, removing the unnecessary parts of the pipe by physical processing or chemical etching.

Since the stent 202 has the notches 225 made at the end portions, deformation of the end portions of the stent, especially local deformation of the end portions is made easier, and hence the response to the deformation of the blood vessel in which the stent is indwelling is inproved. Further, since the ends 223 are armed by the ends of a plurality of frame segments 226a, the ends 223 have a sufficient strength not to collapse. Furthermore, since the holes 224 defined by the frame segments 226a and 226b are made, these holes 4 make easier the deformation of the middle part of each frame section, hence the stent, especially in the direction to which the outside diameter decreases.

The number and shape of the notches and holes are not limited to those shown in FIG. 13. The number of the notches is preferably within the range of about 3 to 10, and that of the holes is also preferably within the same range.

The frame 220 (stent) is within the range of 2.0 to 30 mm, preferably 2.0 to 20 mm in outside, 1.4 to 29 mm, preferably 1.6 to 29.4 mm in inside diameter, and 10 to 150 mm, preferably 15 to 100 mm in length.

The shape of this stent is not limited to that shown in FIG. 13, and may be a shape with trapezoidal notches at the ends and hexagonal holes disposed in a honeycomb pattern in the middle portion, or rectangular notches at the ends and rectangular holes (twice longer than the notches) in the middle.

The super elastic metal fi)r this stent is preferably a super elastic alloy. Super elastic alloy here refers to an alloy which is generally called "a shape-memory alloy" and resumes at the body temperature (around 37° C.) at the highest its original shape after being deformed even to such a degree that an ordinary metal undergoes permanent deformation.

Preferable super elastic alloys are Ti—Ni alloy consisting essentially of 49 to 53 atom percent of Ni, Cu—Zn alloy consisting essentially of 38.5 to 41.5 wt % of Zn, Cu—Zn—X alloy containing 1 to 10 wt % of X (X=Be, Si, Sn, Al or Ga), and Ni—Al alloy consisting essentially of 36 to 38 atom percent of Al. Ti—Ni alloy is especially preferable. The mechanical property of Ti—Ni alloy can be changed as desired by replacing part of Ti—Ni alloy with 0.01 to 30.0 atom percent of X (X=Cu, Pb, or Zr) or selecting the reduction ratio of cold working and/or the conditions of the final heat treatment.

The buckling strength (yielding stress when a load is increased) of the super elastic alloy used is 5 to 200 kg/mm$^2$ (22°), preferably 8 to 150 kg/mm$^2$, and the recovery stress Wielding stress when a load is decreased) is 3 to 180 klmm$^2$ (22° C.), preferably 5 to 130 kg/mm$^2$.

Since the stent 202 of this embodiment is made, for example, by using a pipe of a super elastic metal and removing the parts of the pipe at which the notches or holes are made, it is a single piece without an abrupt change in the physical property within it.

If there is a part at which the physical property changes abruptly, that part deforms differently from the other parts, distorting the shape of the entire stent unnaturally. The distorted shape can cause an unnatural blood flow which can cause a constriction again. There is also the possibility of breaking from that part because of a stress concentration.

However, since the stent of this invention is made as a single piece without an abrupt change in the physical property within it as described above, it has no problems as described above.

The shape of the stent is not limited to the one described above, and may be any other shape which can be impressed to a smaller diameter when put in the body and expand (resume) to the original diameter after being put in the body, for example, coil, circular cylinder, non-circular cylinder, rolt flat-spring coil, cage, or mesh.

The stent used for the stenosis-treating device of this invention may also be the one shown in FIG. 14. The stent 242 comprises a frame 242a which is of a substantially-circular cylinder and can be compressed to a smaller diameter, a layer of a thermoplastic resin with which the frame 242 is coated, and a cylindrical cover 243 which closes the openings in the cylindrical wall of the frame 242a and is bonded to the thermoplastic resin.

The difference between this stent 242a and aforementioned stent 202 is that the stent 242a has the cylindrical cover 243 on either side or both sides of the cylindrical wall. Therefore, the notches and holes in the cylindrical wall are closed by the cover 243, and the entrance of the body tissue into the stent can be prevented. Further, the cylindrical cover 243 is welded to the thermoplastic resin, it does not come off the frame 242a before and after the stent is put in the body.

The stent 202 or 242 made as described above is held by the inside surface of the front end portion of the sheath 203 in a compressed state. Since the stent has a recovering force, it presses against the inside surface of the sheath 203 radially and is held in tight contact with the inside surface of the sheath 203.

The sheath 203 is a tube as shown in FIGS. 10 and 12, and has a front end opening 203 and a rear end opening (not shown) in the front and rear ends. The front end opening 230 is an exit for the stent 202 when the stent 202 is left in the stenosed part out of the sheath 203. The stent 202 put out of the sheath 203 is released from the pressing force, and expands to resume the original shape.

A Y-shaped connector 233 is secured to the rear (distal) end portion provided with a rear opening in the rear end by means of a connector 232 as shown in FIGS. 10 and 15.

This stenosis-treating device has means for locking the sheath 203 with the catheter in a releasable manner (locking mechanism). Specifically, the Y-shaped connector 233 is provided with an adapter 234 at the rear. When this adapter 234 is turned in the clockwise direction, the Y-shaped connector is locked with the outer tube 252 of the balloon catheter 205 passing through it, and the sheath 203 cannot be moved on the balloon catheter 205 in the direction of the axis. When the adapter 234 is turned in the counterclockwise direction, the lock is released, and the sheath 203 becomes free and can be moved on the catheter 205 in the direction of the axis.

Since the stenosis-treating device of this invention has the locking mechanism for locking the sheath and balloon catheter with each other, the balloon catheter and sheath can be inserted into or pulled out of the body together by grasping either one or both of them when they are locked, and releasing of the stent at an unintended place can be prevented. Since the locking mechanism has a releasing mechanism, the sheath can be readily freed from the balloon catheter when necessary, and release of the stent becomes possible.

Specifically, the adapter 234 is a cylinder and has the inside surface which becomes gradually smaller in diameter from the front end rearward. This tapered surface is provided with a thread to make the first screwcoupler 234. The rear end portion of the Y-shaped connector is provided with a plurality of shts 233a extending in the direction of the axis. The outside surface of this rear end portion is tapered and provided with a thread to make the screw-coupler 233b.

When the adapter 234 is turned in the clockwise direction, the coupling of the first and second screw-couplers is tightened, and thereby the inside surface of the rear end portion of the Y-shaped connector is pressed on the outside surface of the outer tube 252 of the balloon catheter 205, locking the sheath 203 with the balloon catheter 205.

When the adapter 234 is turned in the counterclockwise direction, the coupling of the first and second screw-ouplers is loosened, and the locking is released and the sheath 203 can be moved on the balloon catheter 205 in the direction axis.

The locking mechanism is not limited to the construction described above. For example, the first screwcoupler is formed in the tapered surface which is formed in the rear end portion of the Y-shaped connector and becomes gradually larger in inside diameter toward the rear end, and the second screw-coupler is formed on the tapered front end portion of the adapter 234 which becomes gradually smaller in the outside diameter toward the front end and is provided with slots in the direction of the axis.

The Y-shaped connector is preferably provided with means for sealing the space between the sheath 203 and the balloon catheter 205 in the liquid-tight fashion in the inside surface.

The sheath 203 is preferably provided with an X-ray shadow generating part 212 on the outside surface. In this embodiment, an X-ray shadow generating part 212 is disposed on the outside surface of the portion of the sheath in which the stent is held. This X-ray shadow generating part 212 makes it easier to know the position of the sheath 203 under X-rays. Further, when the projection 206 (described later) is made of an X-ray opaque material, the relative position between the sheath 203 and the balloon catheter 205 can be known by the X-ray shadow generating part 212 and the projection 206, and hence the operation of the device is made easier.

Further, the position at which the X-ray shadow generating part 212 is disposed may be the front end of the sheath 203.

When the X-ray shadow generating part 212 is disposed at the position near the projection 206 as in this embodiment, the release of the stent can be performed by watching the X-ray shadow generating part 212 moving away from the projection 206. When the X-ray shadow generating part 212 is disposed at the front end of the sheath 203, on the other hand, the release of the stent can be performed by watching the X-ray shadow generating part 212 moving closer toward the projection 206.

The X-ray shadow generating part can be formed by attaching an appropriate X-ray opaque material (gold, platinum, platinum-iridium alloy, silver, stainless steel, or an alloy of them) on the outside surface of the sheath 206 or burying it in the outside surface or inside surface of the sheath 206. Further, the surface of the sheath 203 is preferably made smooth without steps ar the X-ray shadow generating part 212 is formed.

The sheath 206 is within the range of 1.16 to 4.2 mm, preferably 1.3 to 3.8 mm in outside diameter, within the range of 1.0 to 3.2 mm, preferably 1.1 to 3.0 mm in inside diameter, and within the range of 0.08 to 0.50 mm, preferably 0.10 to 0.3 mm.

In this example, the outside diameter is 1.7 mm, inside diameter is 1.46 mm, wall thickness is 0.12 mm.

The material for the sheath 203 is preferably a thermoplastic elastomer selected from nylon, urethane, polyester, and olefin from the physical properties requested of the sheath (flexibility, rigidity, strength, kink resistance, and elasticity).

Further, the outside surface of the sheath 203 is preferably treated to increase the lubricity.

For this purpose, the outside surface of the sheath 203 may be covered with a hydrophilic polymer, such as poly (2-hydroxyethyl-methacrylate), polyhydroxyethylacrylate, hydroxypropyleellulose, methyl vinyl ether maleic anhyd copolymer, polyethylene glycol polyacrylamide, or polyvinylpyrrolidone by coating or fixing.

The inside surface of the sheath 203 may also be covered with the same material by coating or fixing in order to increase the lubricity against the balloon catheter 205.

Figure 20:
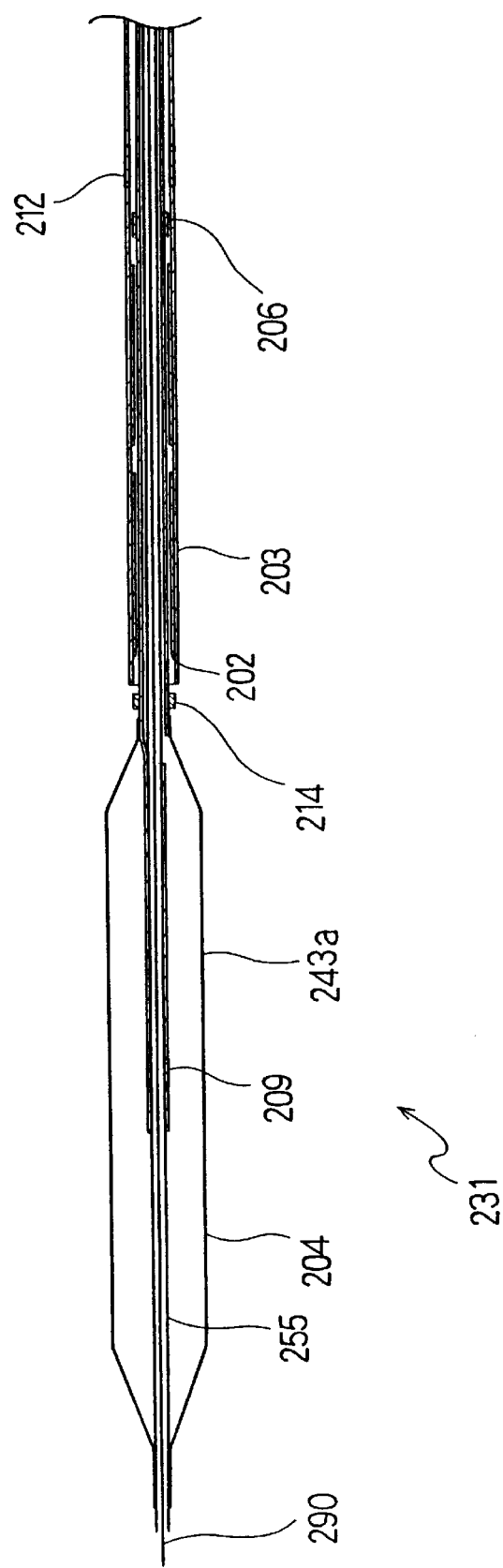
FIG. 20 is a sectional view of the front end portion of another embodiment of the stenosis-treating device of this invention.
Figure 21:
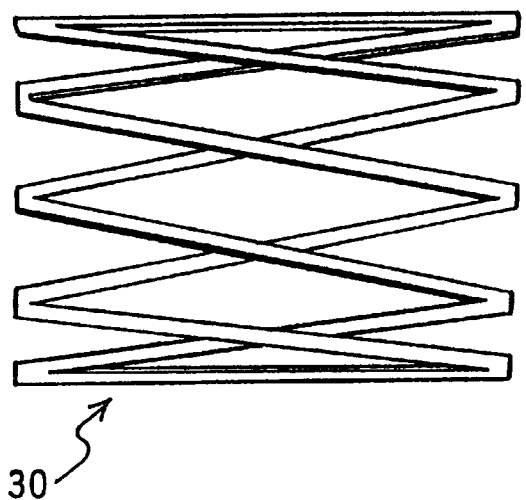
FIG. 21 is a diagrammatic front view of a conventional indwelling stent
Figure 22:
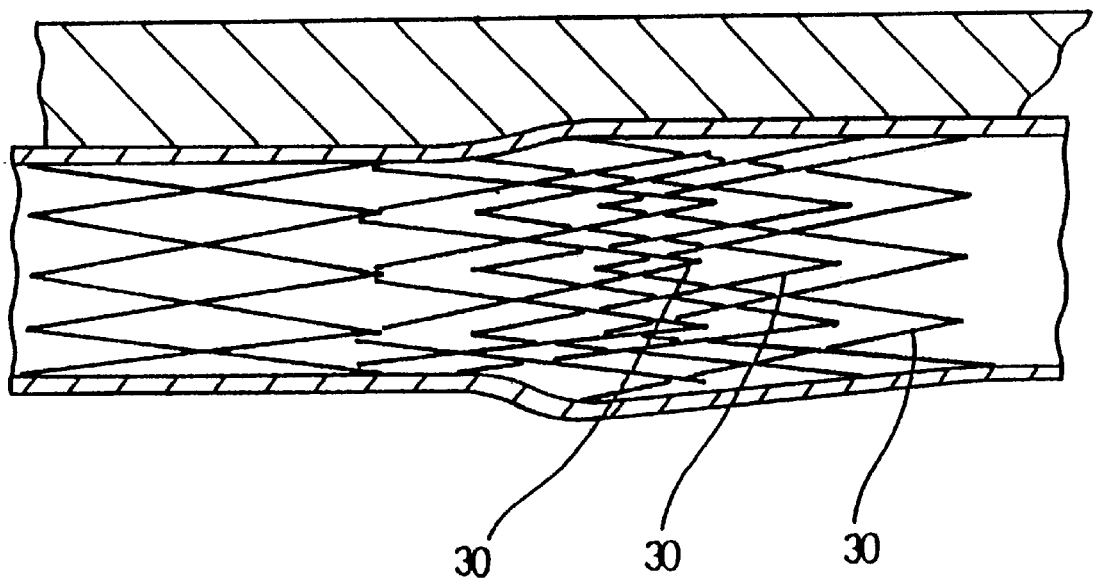
FIG. 22 illustrates the state in which the stent shown in FIG. 21 is used.
Figure 23:
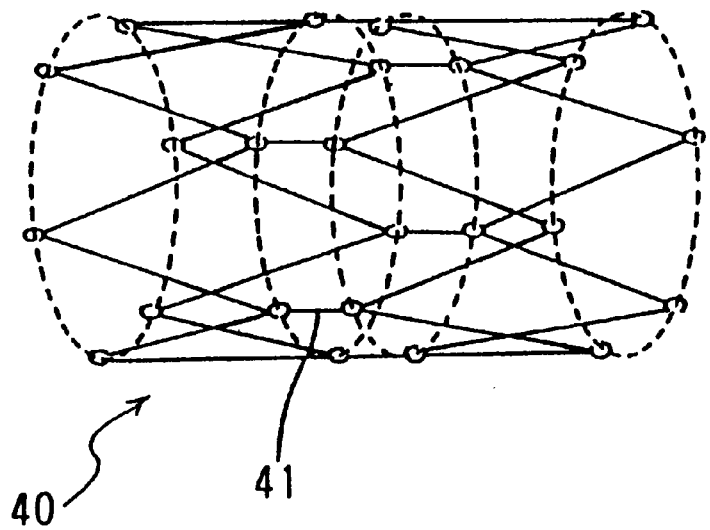
FIG. 23 is a diagrammatic front view of a conventional indwelling stent.

Next, another embodiment of the stenosis-treating device of this invention is described below with reference to FIG. 20.

The difference between the stenosis-treating device 231 of this embodiment and the stenosi-treating device 200 of the embodiment described above is that the balloon catheter 205 of the stenosis-treating device 231 of this embodiment has a balloon protecting means 214 disposed in the rear of the balloon and in the front of the sheath 203. The other constant is the same. The corresponding components of the two stenosis-treating devices are designated by the same reference numbers.

Since the stenosi-treating device 231 of this embodiment has such a balloon protecting means 214, the balloon protecting means 214 comes into contact with the front end of the sheath 203, and the balloon 204 does not enter the inside of the sheath 203 if the balloon catheter 205 alone is pulled rearward or the sheath 203 alone is pushed frontward Therefore, the problem that the balloon can be damaged by the sheath 203 or the stent 202 is solved.

Speceically, the balloon protecting means 214 of this embodiment is a ring-shaped projection which has an outside diameter greater than the inside diameter of the sheath 203. The outside diameter of the balloon protecting means 214 is preferably smaller than the outside diameter of the sheath 203. The balloon protecting means 214 may be formed as a part of the outer tube of the balloon catheter. The balloon protecting means 214 may be made of an X-ray opaque material, and may also be one or more than one separate projections disposed on the outer tube of the balloon catheter.

Next, the use of the stenosis-treating device of this invention is described below with reference to FIGS. 17 to 19.

First, a guide wire 290 is inserted from the first opening 259 of the branched hub 208 and passed through the intended stenosed part 295 by the conventional technique. Next, the stenosis-treating device 200 of this invention is advanced along the guide wire up to a point near stenosed part 295 in a hollow organ 96. The position of the stenosed part is confirmed beforehand, for example, by injecting a contrast medium into the hollow organ from a guiding catheter connected to the entrance of the hollow organ (entrance of coronary arteries, for example).

Next, the stenosis-treating device 200 is carefullly advanced to accurately position the balloon 204 in the stenosed part as shown in FIG. 17(b), then a liquid for inflating a balloon is injected from the second opening 251 to inflate the balloon 204. When inflated, the balloon 204 dilates the stenosed part. Some stenosed parts can be ameliorated up to about 90% though others are not ameliorated at all, depending on the types of stenosis.

The stenosis-treating device of this invention thus can dilate the stenosed part a certain extent before putting the stent in the stenosed part by inflating the balloon in the stenosed part. The position of the balloon is checked from the X-ray shadow producing part 209.

Figure 18A:
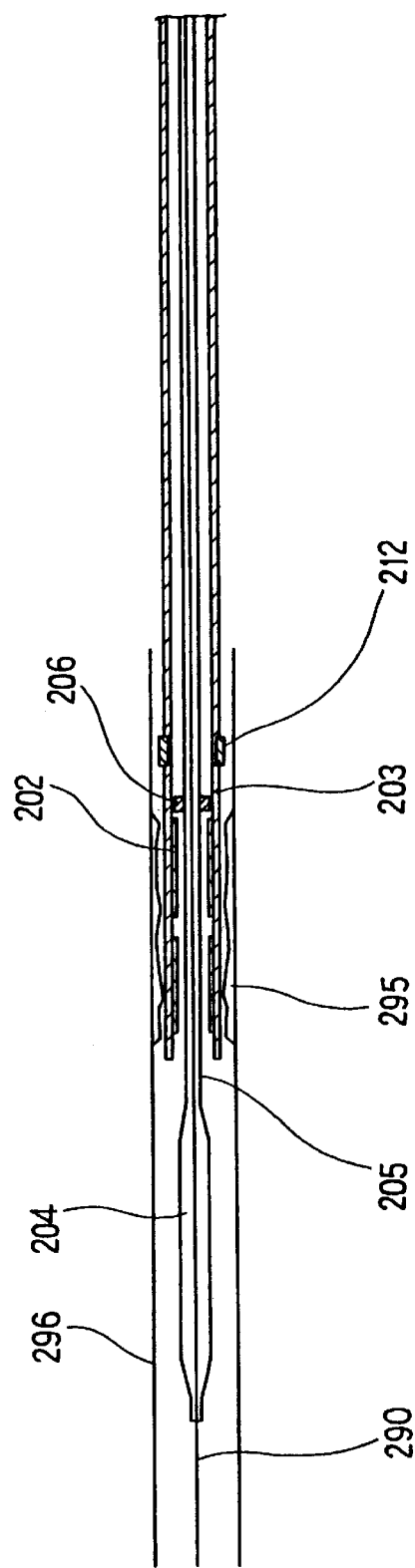
FIGS. 18(a) and 18(b) are diagrammatic sectional views for illustrating the function of the sten -treating device of this invention.
Figure 18B:
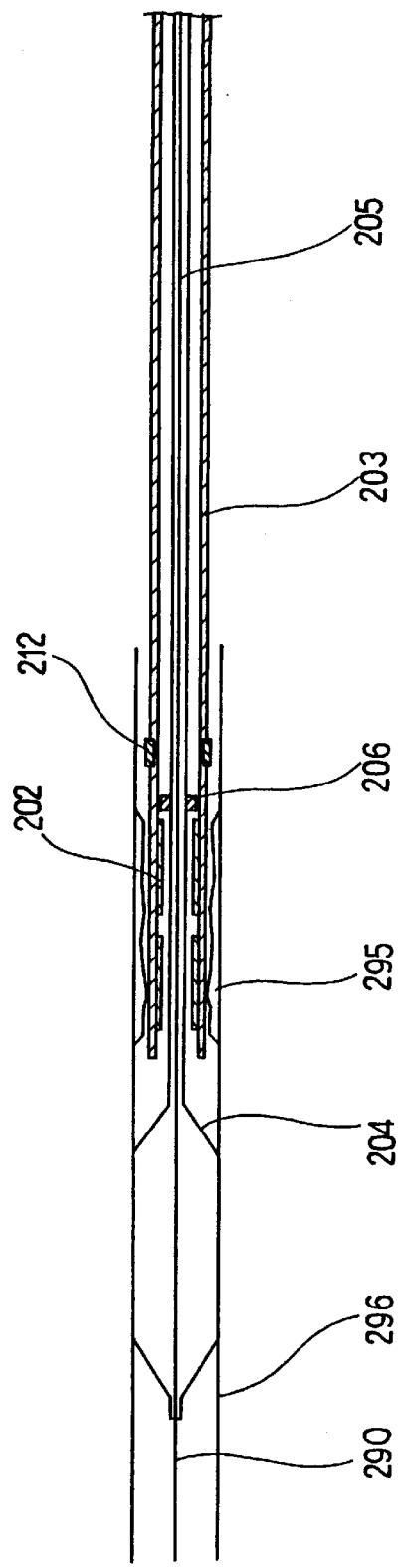

Then, the balloon 204 is deflated, and the stenosis-treating device 200 is further advanced to position the front end portion of the sheath 203 in which the stent 202 is held in the stenosed part 295 as shown in FIG. 18(*a*). This positioning is performed by watching the projection 206 made of an X-ray opaque material by means of X rays. Then the balloon 204 is inflated again and fixed in the hollow organ as shown in FIG. 18(*b*). Thus by inflating the balloon on the fir side of the stenosed part, the stenosis-treating device of this invention can be fixed even in a thin, sharply bending hollow organ as coronary arteries. Therefore, a self-expandable stent can be accurately positioned in the intended stenosed part.

Next, the adapter 234 attached to the Y-shaped connector 233 is turned in the counterclockwise direction to release the locking between the sheath 203 and the balloon catheter 205, and the sheath 203 is moved rearward on the balloon catheter 205. By this move of the sheath 203, the rear end of the stent 202 held in the sheath 203 comes into contact with the projection 206 of the balloon catheter 205, and the stent 202 is left out of the sheath 203 through the front end of the sheath 203. This state is shown in FIG. 19(*a*). The relative position of the sheath 203 to the balloon catheter 205 is known from the X-ray shadow producing part 212 of the sheath 203 and the projection 206 of the balloon catheter made of an X-ray opaque material.

Finally, the balloon is deflated, the balloon catheter 205 together with the sheath 203 is pulled out from the hollow organ 96.

As describe above, the stenosis-treating device of this invention makes it possible to put a self-expandable stent accurately and easily in an intended stenosed part even in a thin, sharply bending blood vessel as coronary arteries by the simple construction.

Next, concrete examples of the stent of this invention are described blow.

EXAMPLE 1

A super elastic metal pipe, 7.8 mm in outside diameter, 7.0 mm in inside diameter and about 15 mm in length, was prepared by cold-drawing an alloy pipe of Ti—Ni alloy (Ni: 51 atom%).

Next, an unfinished stent (frame) as shown in FIG. 1 was made of the pipe by using an NC electric-disharge machine (equipped with A3R rotary head) manufactured by SOLDIC with the super elastic metal pipe on the movable side and the metal template on the fixed side. This discharge processing was performed with the processing current of 2A and the servo voltage of 3 to 4 V. The width of the frame segment 6*a* shown in FIG. 1 of the frame obtained by this processing was 0.45 mm.

Next, the frame stent was blasttreated using glass beads 15 to 30 $\mu$m in diameter under a pressure of 2 to 3 kg/cm$^2$. The frame was rid of edges and burrs by this blast treatment As the result, the width of the frame segment 6*a* shown in FIG. 2 became to 0.40 mm.

Next, the thermally denaturalized parts occurring on the outside surface and around the removed parts during the electric-discharge processing were removed This process was permitted by removing the outside surface of the frame by chemical etching which immersed the frame or about 2 minutes in a treatment liquid (about 40° C.) prepared by mixing fluoric acid and nitric acid and adding a little amount of hydrogen peroxide. The shape of the frame after this chemical etching was as shown in FIG. 1. The average outside diameter was 7.6 mm, the average wall thickness was 0.19 mm, and the average width of the frame segment 6*a* was 0.35 mm.

This finished stent resumed the manufactured shape after it was deformed by fingers. Therefore, the thermally denaturalized parts (the parts which do not exhibit super elastic) were almost all removed.

This stent can be used for ameliorating iliac artery, femoral artery and bile duct.

EXAMPLE 2

A super elastic metal pipe, 4.2 mm in outside diameter, 3.6 mm; in inside diameter and about 15 mm in length, was prepared by cold-drawing an alloy pipe of Ti—Ni alloy (Ni: 51 atom%).

This pipe was then subjected to laser processing by using YAG laser machine (ML-4140A, manufactured by Miyachi Tecnos). This laser processing was performed by inserting a stainless-steel mandrel 3.6 mm in diameter and 100 mm in length, into the pipe, and two time of repetition of shining laser light under the operating condition (electric current: 16 A, Operating speed: 10 mm/min). By this laser processing, an unfinished stent (frame) consisting of two identical stents connected with each other as shown in FIG. 2 was made. The average wire diameter of this frame was 0.35 mm.

Next, the frame was blast-treated using glass beads 15 to 30 $\mu$m in diameter under a pressure of 2 to 3 kg/cm$^2$. The frame was rid of edges and burrs by this blast treatment. As the result, the average wire diameter of the frame became 0.31 mm.

Next, the thermally denaturalized portions in the periphery of the wires which occurred during the laser processing were removed. This process was performed by removing the outside surface of the frame by chemical etching which immersed the frame for about 2 minutes in a treatment liquid (about 40° C.) prepared by mixing fluoric acid and nitric acid and adding a little amount of hydrogen peroxide. The shape of the frame after this chemical etching was as shown in FIG. 1. The average outside diameter was 4.06 mm and the average wire diameter was 0.15 mm.

This finished stent resumed the manufactured shape after it was deformed by fingers. Therefore, the thermally denaturalized parts (the parts which do not exhibit super elastic) were almost completely removed. This stent can be used for ameliorating coronary arteries.

EXAMPLE 3

The stent made in example 2 was gold-plated on the entire surface to increase the biocompatibility.

This gold plating was performed by immersing the stent made in example 2 in the plating bath by dissolving potassium cyanoaurate in a sulfamic acid derivative plating bath product name: Auroflex T1, Tokurikihonten) heated to about 40° C. By this process, a lusterless gold-plate layer of 1.8 $\mu$m was formed on the surface of the stent.

This stent can also be used for ameliorating coronary arteries as the stent of example 2.

EXAMPLE 4

A super elastic metal pipe, 4.2 mm in outside diameter, 3.6 mm inside diameter and about 15 mm in length, was prepared by cold-drawing an alloy pipe of Ti—Ni alloy (Ni: 51 atom%).

This super elastic metal pipe was degreased and cleansed by first immersing the pipe in an aqueous solution of a surface-active agent and next in RO water, and after drying the pipe, immersing it in hexane.

The super elastic metal pipe was dipped in a photoresist solution (positive photoresist, product name: OFPR-800, Tokyookakogyo), and a coating of about 2 $\mu$m in thickness was formed on the inside and outside surfaces. This pipe was prebaked at 85° C. for 30 minutes.

A masking film was prepared by cutting away the parts corresponding to those parts of the pipe at which notches or holes are to be made. This film was wound on the outside surface of the pipe and put into tight contact with the surface of the pipe by suction.

The pipe was then subjected to the exposing process. This exposing was performed by using an extra-high voltage mercury-are lamp with an output power 3 mW and luminous exposure 250 mJ/cm for 15 seconds rotating the pipe at a speed of 300 rpm.

Next, the pipe was immersed in a developer (product name: NMP, Tokyookakogyo) for development. Then, the pipe was postbaked at 130° C. for 30 minutes.

Next, an etching liquid was prepared by mixing distilled water 20 ml, glycerol 45 ml, nitric acid (specific gravity: 1.40) 25 ml, and fluoric acid (40%) 1 ml.

The pipe with the developed photoresist was immersed in this etching liquid heated to about 40° C. for about 20 minutes.

The pipe was then dipped in aceton to dissolve the photoresist. Thus, the parts at which notches or holes to be made were removed from the super elasic metal pipe, and an unfinished stent(frame) of the shape as shown in FIG. 2 was obtained The wire diameter b of this fame was 0.32 mm.

The frame has side edges peculiar to wet etching formed by the above etching process. To remove the side edges, the frame was blast-treated by using Next, the frame was blasttreated by using glass beads 15 to 30 $\mu$m in diameter under a pressure of 2 to 3 kg/cm$^2$. The frame was rid of edges and burrs by this blast treatment.

To improve the surface condition, the blast-treated frame was further subjected to a surface treatment, which chemically etched the surface by immersing the frame for about 2 minutes in a surface-treating liquid (about 40° C.) prepared by mixing fluoric acid and nitric acid and adding a little amount of hydrogen peroxide.

The frame after this chemical etching (finished stent) was as shown in FIG. 2. The average outside diameter was 4.12 mm and the average wire diameter was 0.28 mm.

This stent resumed the manufactured shape after it was deformed by fingers. Therefore, the thermally denaturalized parts (the parts which do not exhibit super elastic) were almost completely removed.

This stent can be used for ameliorating coronary arteries.

EXAMPLE 5

A super elastic metal pipe, 7.5 mm in outside diameter, 7.0 mm in inside diameter and about 50 mm in length, was prepared by cold-drawing an alloy pipe of Ti—Ni alloy (Ni: 51 atom%).

This pipe was then subjected to laser processing by using YAG laser machine SL116E (equipped with a X-Y table) manufactured by NEC under the operating condition of an electric current 29 A, speed 10 mm/min., and Q switching frequency 1 kHz rotating the pipe.

Next, the unfinished stent (frame) was blast-treated using glass beads 15 to 30 $\mu$m in diameter under a pressure of 2 to 3 kg/cm$^2$. The frame was rid of edges and burrs by this blast treatment.

Next, the thermally denaturalized portions in the periphery of the wire segments which occurred during the laser processing were removed. This process was performed by chemical etch which inmersed the frame for about 2 minutes in a treatment liquid (about 40° C.) prepared by mixing fluoric acid and nitric acid and adding a little amount of hydrogen peroxide.

By this chemical etching, the wire segments became substantially rectangular with the edges removed in cross section.

The wires in the middle portion were 0.4 mm in wire diameter and 0.092 cm$^2$ in cross-sectional area [0.4 (wire diameter: length of the horizontal sides of the rectangle)× 0.23 (thickness: length of the vertical sides of the rectangle)].

The wires in both side portions were 0.3 mm in wire diameter and 0.039 cm$^2$ in cross-sectional area [0.3 (wire diameter: length of the horizontal sides of the rectangle)× 0.13 (thickness: length of the vertical sides of the rectangle)].

The ratio of the wire diameters (middle portion: end portion)=1.3:1.

The ratio of the cross sectional areas (middle portion: end portion )=2.4:1.

The recovering force of the finished stent of this example was measured by depressing the middle point and both ends of the stent 2 mm with a push-pull gauge. The recovering force was 370 g at the middle point and 150 g at both end. The stent resumed to the manufactured shape when the pressure was removed This stent can be used for ameliorating coronary arteries.

EXAMPLE 6

The stent made in example 5 was gold-plated on the entire surface to increase the biocompatbility.

This gold plating was performed by immersing the stent made in example 1 in the plating bath prepared by dissolving potassium cyanoaurate in a sulfamic acid derivative plating bath (product name: Auroflex T1, Tokurikihonten) heated to about 40° C. By this process, a lusterless gold-plate layer of 1.8 $\mu$m was formed on the surface of the stent.

This stent can also be used for ameliorating coronary arteries as the stent of example 1.

I claim:

1. A stent comprising a metal frame structure having a substantially circular cylindrical shape which is compressible to a smaller outside diameter for placement in a portion of a body and which is self-expandable from the smaller outside diameter after placement in the portion of thereby, said frame structure being a single piece of metal material without abrupt changes in physical properties of the metal frame structure and without any welded or soldered portions by removing portions of a super elastic metal pipe, said frame structure comprising wire segments in a shape of a repeating "<" which extend helically to form the substantially circular cylindrical shape of the frame structure.

2. A stent of claim 1, wherein said wire segments include two wire segments wound in parallel in a helix to form the circular cylindrical shape of the frame structure.

3. A stent of claim 1, wherein said frame structure is coated with a biocompatible material.

4. A stent of claim 1, wherein said wire segments are connected at a plurality of spaced apart locations.

5. A stent of claim 1, wherein said frame structure is a wire structure having wire segments.

6. A stent of claim 5, wherein said wire structure includes opposite ends, the wire structure possessing a cross-sectional area that becomes gradually smaller towards the respective ends.

7. A stent of claim 5, wherein said wire structure includes two wire segments connected with each other at at least two points.

8. A stent of claim 5, wherein said wire structure is formed of two wire segments disposed in parallel with each other to form a helix structure of two parallel wire segments, and said two wire segments forming an angle α of the helix structure with respect to an axis of the wire structure that is smaller than an angle β made by a wire segment with respect to an axis of a helix structure formed of a single wire segment.

9. A stent of claim 5, wherein said stent has an outside surface that is chamfered.

10. A stent of claim 5, wherein said stent includes a middle portion and an end portion on each side of the middle portion, the wire segments in the middle portion being relatively large in cross section and the wire segments in the end portions being relatively smaller in cross section.

11. A stent of claim 1, wherein said stent has an outside surface that is chamfered.

12. A stent of claim 1, wherein said frame structure possesses a zigzag shape that extends helically.

13. A stent of claim 1, wherein said frame structure is comprised of two parallel zigzag shaped portions that extend helically.

14. A stent of claim 1, wherein said frame structure is comprised of two parallel zigzag shaped portions that extend helically, with an end of each zigzag shaped portion being connected to one another.

15. A stent comprising a frame structure having a substantially circular cylindrical shape which is compressible to a smaller outside diameter for placement in a portion of a body and which is self-expandable from the smaller outside diameter after a placement in the portion of the body, said frame structure being formed as a single piece of material without abrupt changes in physical properties of the frame structure and without any welding portions and any soldering portions by removing portions of a Ti—Ni alloy pipe, said frame structure possessing a zigzag shape that extends helically.

16. A stent of claim 15, wherein said frame structure is comprised of two parallel zigzag shaped portions that extend helically.

* * * * *

UNITED STATES PATENT AND TRADEMARK OFFICE
CERTIFICATE OF CORRECTION

PATENT NO. : 6,013,854
DATED : January 11, 2000
INVENTOR(S) : Yousuke MORIUCHI

It is certified that error appears in the above-identified patent and that said Letters Patent is hereby corrected as shown below:

In Column 1, line 20, after "has" insert -- the --.
In Column 1, line 53, delete "desen bed" and insert -- described --.
In Column 2, line 29, before "flexibility" insert -- sufficient --.
In Column 2, line 61, delete "boon-expandable" and insert -- balloon-expandable --.
In Column 3, line 5, delete "in" and insert -- since --.
In Column 3, line 14, delete "fbr" and insert -- for --.
In Column 3, line 52, delete "stentinserting" and insert -- stent-inserting --.
In Column 5, line 12, delete "sten-reacting" and insert -- stenosis-reacting --.
In Column 5, line 51, delete "mele" and insert -- middle --.
In Column 5, line 63, delete "firmed" and insert -- formed --.
In Column 6, line 9, delete "in" and insert -- fan --.
In Column 6, line 38, delete "preforably" and insert -- preferably --.
In Column 6, line 59, delete "yielding" and insert -- (yielding --.
In Column 8, line 2, delete "electmplating" and insert -- electroplating --.
In Column 8, lines 13-14, delete "sufficently" and insert -- sufficiently --.
In Column 8, line 45, delete "iameter" and insert -- diameter --.
In Column 9, line 34, delete "uv" and insert -- UV --.
In Column 9, line 36, delete "photoresit" and insert -- photoresist --.
In Column 10, line 65, delete "a so" and insert -- also --.
In Column 10, line 66, delete "wire" and insert -- wires --.
In Column 11, line 3, after "has" delete "a".
In Column 11, line 5, delete "ibrmed" and insert -- formed --.
In Column 11, line 9, delete "hyperpi" and insert -- hyperplasia --.
In Column 11, line 10, delete "steno" and insert -- stenosis --.

UNITED STATES PATENT AND TRADEMARK OFFICE
CERTIFICATE OF CORRECTION

PATENT NO. : 6,013,854
DATED : January 11, 2000
INVENTOR(S) : Yousuke MORIUCHI

It is certified that error appears in the above-identified patent and that said Letters Patent is hereby corrected as shown below:

In Column 13 line 22, after "and" delete "e".
In Column 13, line 23, delete "during" and insert – extruding --.
In Column 13, line 26, delete "theses" and insert – thickness --.
In Column 13, line 44, delete "chained" and insert – chamfered --.
In Column 13, line 44, delete "of" and insert – from --.
In Column 13, line 51, delete "silecone" and insert – silicone --.
In Column 13, line 63, delete "ibrms" and insert – forms --.
In Column 14, line 6, delete "hydlroxymethylmethacrylate" and insert – hydroxyethylmethacrylate --.
In Column 14, line 6, delete "HMA-" and insert – HEMA --.
In Column 14, line 29, delete "predetermine" and insert – predetermined --.
In Column 14, line 30, delete "chemically the pipe physically" and insert – the pipe physically or chemically --.
In Column 14, line 32, delete "layer" and insert – laser --.
In Column 15, line 26, delete "laser" and insert – Laser --.
In Column 15, line 33, delete "degresed" and insert – degreased --.
In Column 15, line 51, delete "peribrned" and insert – performed --.
In Column 16, line 35, delete "1hr" and insert – for --.
In Column 17, line 57, delete "balon" and insert – balloon --.
In Column 18, line 37, delete "maintainabdity" and insert – maintainability --.
In Column 18, line 38, delete "elasticit" and insert – elasticity --.
In Column 18, line 58, delete "Chion" and insert – fashion --.
In Column 19, line 48, delete "nrgidity" and insert – rigidity --.
In Column 20, line 44, delete "(old," and insert – gold, --.
In Column 20, line 66, delete "sta steel" and insert – stainless steel --.

UNITED STATES PATENT AND TRADEMARK OFFICE
CERTIFICATE OF CORRECTION

PATENT NO. : 6,013,854
DATED : January 11, 2000
INVENTOR(S) : Yousuke MORIUCHI

It is certified that error appears in the above-identified patent and that said Letters Patent is hereby corrected as shown below:

In Column 21, line 33, delete "fi)r" and insert -- for --.
In Column 23, line 2, delete "shts" and insert -- slits --.
In Column 24, line 11, delete "anhyd" and insert -- anhydride --.
In Column 24, line 26, delete "constant" and insert -- construction --.
In Column 25, line 16, delete "fir" and insert -- far --.
In Column 28, line 55, delete "thereby," and insert -- the body, --.

Signed and Sealed this

Twenty-sixth Day of December, 2000

Attest:

Q. TODD DICKINSON

*Attesting Officer*          *Director of Patents and Trademarks*